(12) United States Patent
Trnka et al.

(10) Patent No.: US 11,185,587 B2
(45) Date of Patent: Nov. 30, 2021

(54) PHARMACEUTICAL COMPOSITION CONTAINING A MIXTURE OF PROENZYMES AND ENZYMES

(71) Applicants: Frantisek Trnka, Ceske Budejovice (CZ); Pavel Dolezal, Hradec Kralove (CZ)

(72) Inventors: Frantisek Trnka, Ceske Budejovice (CZ); Pavel Dolezal, Hradec Kralove (CZ)

(*) Notice: Subject to any disclaimer, the term of this patent is extended or adjusted under 35 U.S.C. 154(b) by 102 days.

(21) Appl. No.: 16/281,130

(22) Filed: Feb. 21, 2019

(65) Prior Publication Data
US 2019/0247471 A1    Aug. 15, 2019

Related U.S. Application Data

(62) Division of application No. 15/037,331, filed as application No. PCT/CZ2014/000133 on Nov. 12, 2014, now abandoned.

(30) Foreign Application Priority Data

Nov. 18, 2013 (CZ) .............................. CZ2013-891

(51) Int. Cl.
| | |
|---|---|
| A61K 45/06 | (2006.01) |
| A61K 38/46 | (2006.01) |
| A61K 38/48 | (2006.01) |
| A61K 47/34 | (2017.01) |
| A61K 47/38 | (2006.01) |
| A61K 9/00 | (2006.01) |
| A61K 9/02 | (2006.01) |
| A61K 9/70 | (2006.01) |
| A61K 47/10 | (2017.01) |
| A61K 47/26 | (2006.01) |

(52) U.S. Cl.
CPC .............. *A61K 45/06* (2013.01); *A61K 9/006* (2013.01); *A61K 9/0019* (2013.01); *A61K 9/0031* (2013.01); *A61K 9/0075* (2013.01); *A61K 9/0078* (2013.01); *A61K 9/02* (2013.01); *A61K 9/70* (2013.01); *A61K 38/465* (2013.01); *A61K 38/4826* (2013.01); *A61K 47/10* (2013.01); *A61K 47/26* (2013.01); *A61K 47/34* (2013.01); *A61K 47/38* (2013.01); *C12Y 301/01003* (2013.01); *C12Y 302/01001* (2013.01); *C12Y 304/21001* (2013.01); *C12Y 304/21004* (2013.01)

(58) Field of Classification Search
None
See application file for complete search history.

(56) References Cited

U.S. PATENT DOCUMENTS

| | | | |
|---|---|---|---|
| 4,514,388 | A | 4/1985 | Psaledakis |
| 5,858,357 | A | 1/1999 | Trnka et al. |
| 7,049,484 | B2 | 5/2006 | Howard et al. |
| 2008/0299185 | A1 | 12/2008 | Ortenzi et al. |
| 2011/0123605 | A1 | 5/2011 | Ortenzi |
| 2012/0251516 | A1 | 10/2012 | Kenyon et al. |
| 2013/0244920 | A1 | 9/2013 | Lee et al. |

FOREIGN PATENT DOCUMENTS

| | | |
|---|---|---|
| AU | 2010310887 | 6/2012 |
| CN | 102949712 A | 3/2013 |
| CZ | 19951272 | 5/1995 |
| CZ | 1995-1272 A3 | 12/1996 |
| CZ | 283972 | 7/1998 |
| CZ | 303244 | 6/2012 |
| CZ | 307195 B6 | 3/2018 |
| EA | 033123 B1 | 8/2019 |
| EP | 0215662 | 3/1987 |
| EP | 0743070 | 11/1996 |
| EP | 2490711 | 8/2012 |
| EP | 3071218 B1 | 10/2018 |
| IN | 353055 | 11/2014 |
| JP | 2003-513931 A | 4/2003 |
| JP | 6568095 B2 | 8/2019 |
| WO | WO 2008/102264 | 8/2008 |

OTHER PUBLICATIONS

Jemal A. et al., ,,Global Cancer Statistics CA: Cancer J. Clinic., vol. 61, No. 2 p. 69-90, Mar.-Apr. 2011.
Wu. "A new classification system of anticancer drugs—Based on cell biological mechanisms", Medical Hypotheses, vol. 66, pp. 883-887, Jan. 2006.
Downward, J., "The ins and outs of signaling", Nature, vol. 411, pp. 759-762, Jun. 14, 2001.
Wells, J.A., McClendon, C.L., "Reaching for high-hanging fruit in drug discovery at protein-protein interfaces", Nature vol. 450, Dec. 13, 2007, pp. 1001-1009.

(Continued)

*Primary Examiner* — Michelle F. Paguio Frising
(74) *Attorney, Agent, or Firm* — Mark S. Cohen; Pearl Cohen Zedek Latzer Baratz LLP

(57) ABSTRACT

Pharmaceutical composition containing a mixture of proenzymes and enzymes, containing proenzymes trypsinogen and chymotrypsinogen and enzymes α-amylase and lipase as active substances, and one or more pharmaceutically acceptable excipients, for simultaneous, separate and subsequent administration of the composition in parenteral or transmucosal way, the composition has anti-proliferative and anti-metastatic effects to cancer tumours and is intended for therapeutic, prophylactic and anti-metastatic use in mammals.

23 Claims, 8 Drawing Sheets

Specification includes a Sequence Listing.

(56) References Cited

OTHER PUBLICATIONS

O'Driscoll, L., "Editorial [Hot Topic: Mechanisms of Drug Sensitivity and Resistance in Cancer (Guest Editor: Lorraine O'Driscoll)]", Current Cancer Drug Targets, vol. 9, No. 3, May 2009, pp. 250-251. Abstract only.
Gonzalez-Angulo, A.M et al.,"Overview of resistance to systemic therapy in patients with breast cancer.", Adv. Exp. Med. Biol., vol. 608, 2007, pp. 1-22.
Jemal, A. et al., "Cancer Statistics, 2010", CA Cancer J. Clin., vol. 60, No. 5, Sep.-Oct. 2010, pp. 277-300.
Hemminki, K., "Power and limits of modern cancer diagnostics: cancer of unknown primary", Annals of Oncology., vol. 23, No. 3, Mar. 2012, pp. 760-764.
Lowenthal, R. M.; Eaton, K., Hematol. "Toxicity of Chemotherapy", Hematology/Oncology Clinics of North America ., vol. 10, No. 4, Aug. 1996, pp. 967-990.
Redmond, K. M. et al., "Resistance mechanisms to cancer chemotherapy", Frontiers in Bioscience, 13, May 1, 2008, pp. 5138-5154.
Wu, Ch.-P. et al. "Discovering Natural Product Modulators to Overcome Multidrug Resistance in Cancer Chemotherapy", Curr. Pharm. Biotechnol., vol. 12, No. 04, Apr. 2011, pp. 609-620.
Glickman, M.S., Sawyers, C., "Converting Cancer Therapies into Cures: Lessons from Infectious Diseases", Cell, vol. 148, Mar. 16, 2012, pp. 1089-1098.
Gorre, M.E. et al., "Clinical Resistance to STI-571 Cancer Therapy Caused by BCR-ABL Gene Mutation or Amplification", Science, vol. 293, Aug. 3, 2001, pp. 876-880.
Yang, J. A.; "A Pathway to Follow-On Biologies", Hastings Sci. Tech. L. J., 3, 2011, 217, pp. 1-18.
Borges, S. et al.; "Quantitative effect of CYP2D6 genotypeand inhibitors on tamoxifen metabolism: Implication for optimization of breast cancer treatment", Clin. Pharmacol. Ther. Vol. 80, No. 1, Jul. 2006, pp. 61-74.
Barbosa, M.D.F.S., "Immunogenicity of biotherapeutics in the context of developing biosimilars and biobetters" Drug Discovery Today, vol. 16, No. 7/8, Apr. 2011, pp. 345-353.
Wager K., Jones, G. "The Forward Path for Biopharmaceuticals and Biosimilars: Emerging Options in the Selection of Host Cell Systems", Current Biotechnology. vol 1. No. 4, Aug. 2012, 297-317.
Singh, S. K., "Impact of Product-Related Factors on Immunogenicity of Biotherapeutics", Journal of Pharmaceutical Sciences, vol. 100, No. 2, Feb. 2011, pp. 354-387.
Sachlos,E., et al., "Identification of Drugs Including a Dopamine Receptor Antagonist that Selectively Target Cancer Stem Cells", Cell, vol. 149, Jun. 8, 2012, pp. 1284-1297.
Soundarajan, R., Rao, J.: "Trophoblast 'pseudo-tumorigenesis': Significance and contributory Factors", Reproductive Biology and Endocrinology, vol. 2, No. 15, Mar. 25, 2004, pp. 15-26.
Beard, J., Lancet, "The Cancer Problem", The Lancet, Feb. 4, 1905, pp. 281-283.
Goeth, R.A., J. "Pancreatic Treatment Of Cancer, With Report Of A Cure", Am. Med. Assoc. Mar. 23, 1907 pp. 1030.
Gruchot, Ch., "The Trophoblast of Cancer (John Beard, 1857-1924) Revisited", Oncology vol. 31, 1975, pp. 310-333.
Novak, J., Trnka, F. "Proenzyme Therapy of Cancer", Anticancer Research, vol. 25, Mar. 2005, pp. 1157-1177.
Currie, G.A., Bagshawe, K.D., "The Role of Sialic Acid in Antigenic Expression: Further Studies of the Landschutz Ascites Tumour", Brit J Cancer, vol. 22 No. 4, Dec. 1968, pp. 843-853.
Lah, T. T. et al., "Antiprotease therapy in cancer: hot or not?", Expert Opinion on Biological Therapy , vol. 6, No. 3, Feb. 27, 2006, pp. 257-279.
Bohe, H. et al., "Quantification of pancreatic secretory trypsin inhibitor in colonic carcinoma and normal Adjacent colonic mucosa" J. Clin. Pathol. Vol. 45, No. 12, Dec. 1992, pp. 1066-1069.
Novak, J.F., Trnka, F., Chernin, "Trypsin/chymotrypsin and their respective zymogens inhibit tumor growth in vitro and in vivo", M.I., AACR Meeting Abstracts, vol. 47, Apr. 15, 2006; pp. 1023-1024.
Yamashita, K. et al., "A Tumor-suppressive Role for Trypsin in Human Cancer Progression", Cancer Res., vol. 63, Oct. 15, 2003, pp. 6575-6578.
Fedrowitz, M. et al., "Salivary α-amylase exhibits antiproliferative effects in primary cell cultures of rat mammary epithelial cells and human breast cancer cells", J. Exp. Clin. Cancer Res., vol. 30, No. 102, Oct. 25, 2011, pp. 102-114.
Itkonen, O., Scandin. "Human trypsinogens in the pancreas and in cancer", J. Clin. Lab. Invest., vol. 70, No. 2, Apr. 2010, pp. 136-143.
Koskensalo, S. et al. "Tumour-Associated Trypsin Inhibitor TATI Is a Prognostic Marker in Colorectal Cancer", Oncology, vol. 82, No. 04, Apr. 12, 2012, pp. 234-241.
Nomura, D. K. et al., "Monoacylglycerol Lipase Regulates a Fatty Acid Network that Promotes Cancer Pathogenesis", Cell, vol. 140, No. 1, Jan. 8, 2010, pp. 49-61.
Aub, J.C. Tieslau, C., "Reactions of Normal and Tumor Cell Surfaces To Enzymes. I. Wheat-Germ Lipase and Associated Mucopolysaccharides" Natl. Acad. Sci. USA, vol. 50, Oct. 1963, pp. 613-619.
Willey, K.P. et al., "Functionally Distinct Agonist and Receptor-binding Regions in Human Chorionic Gonadotropin", J. Biol. Chem., vol. 264, No. 33, Nov. 25, 1989, pp. 19716-29.
Acevedo H.F. et al., "Flow Cytometry Method for the Analysis of Membrane-Associated Human Chorionic Gonadotropin, Its Subunits, and Fragments on Human Cancer Cells " Cancer, vol. 69, No. 07, Apr. 1, 1992, pp. 1818-1828.
Acevedo H.F. et al., "Human Chorionic Gonadotropin-Beta Subunit Gene Expression in Cultured Human Fetal and Cancer Cells of Different Types and Origins", Cancer, vol. 76, No. 8, Oct. 1995, pp. 1467-1475.
Acevedo H.F. et al. "Metastatic Phenotype Correlates with High Expression of Membrane-Associated Complete P-Human Chorionic Gonadotropin In Vivo", Cancer. Dec. 1, 1996; vol. 78 No.11, pp. 2388-2399.
Regelson W., "Have We Found the "Definitive Cancer Biomarker"?", Cancer, vol. 76, No. 8, Oct. 1995, pp. 1299-1301.
Illes R.K. "Ectopic hCGbeta expression by epithelial cancer: malignant behaviour, metastasis and inhibition of tumor cell apoptosis." Mol. Cell. Endocrinol., pp. 260-262 and 264-270. Jan. 7, 2007.
Varki, N.M., Varki, A., "Diversity in cell surface sialic acid presentations: implications for biology and disease", Lab. Invest. vol. 87, No. 9, Sep. 2007, pp. 851-857.
Nguyen, D.H., et al. "Effects of Natural Human Antibodies against a Nonhuman Sialic Acid That Metabolically Incorporates into Activated and Malignant Immune Cells1", J. Immunol. Jul. 1, 2005; vol. 175 No. 1 pp. 228-236.
Jungo, C., Marison, I., von Stockar, U."Optimisation of culture conditions with respect to biotin requirement for the production of recombinant avidin in Pichia pastoris", J., Biotechnol., Jan. 20, 2007, vol. 127 No. 4, pp. 703-715.
Paulová, L. et al., "Use of a mixture of glucose and methanol as substrates for the production of recombinant trypsinogen in continuous cultures with Pichia pastoris Mut+", J. Biotechnology., vol. 157 No. 1, Jan. 2012, pp. 180-188.
Kraut, J., "Serine Proteases: Structure and Mechanism of Catalysis", Annual Review Biochemistry. vol. 46, Jul. 1977, pp. 331-358.
Prabhakar, S. S., Muhlfelder, T., "Antibodies to recombinant human erythropoietin causing pure red cell aplasia", Clin. Nephrology, vol. 47, No. 5, May 1997, pp. 331-335.
Öberg, K. et al., "Treatment of Malignant Carcinoid Tumors With Recombinant Interferon alfa-2b: Development of Neutralizing Interferon Antibodies and Possible Loss of Antitumor Activity", J. Natl. Cancer Inst. Vol. 81 No. 7, Apr. 5, 1989, pp. 531-535.
Maury, M. et al., "Spray-drying of proteins: effects of sorbitol and trehalose on aggregation and FT-IR amide I spectrum of an immunoglobulin G", European Journal of Pharmaceutics and Biopharmaceutics., vol. 59, No. 2, Feb. 2005, pp. 251-261.
Wang, "Lyophilization and development of solid protein pharmaceuticals", Int. J. Pharm, Aug. 10, 2000, vol. 203 No. 1-2, pp. 1-60.
Hauss, D.J., "Oral lipid-based formulations", Adv. Drug Deliv. Rev., vol. 59, No. 7, Jul. 30, 2007, pp. 667-676.
Tan, A., Rao, S., "Transforming Lipid-Based Oral Drug Delivery Systems into Solid Dosage Forms: An Overview of Solid Carriers,

(56) References Cited

OTHER PUBLICATIONS

Physicochemical Properties, and Biopharmaceutical Performance", Prestidge, C. A.; Pharm. Res., Dec. 2013, vol. 30, No. 12, pp. 2993-3017.

Mansour, H.M., et al. Characterization of the in situ structural and interfacial properties of the cationic hydrophobic heteropolypeptide, KL4, in lung surfactant bilayer and monolayer models at the air-water interface: implications for pulmonary surfactant delivery. Mol. Pharm., Sep-Oct. 2008, vol. 5, No. 5, pp. 681-695.

Meryman H.T.; "Cryoprotective Agents", Cryobiology vol. 8, Issue 2, Apr. 1971, pp. 173-183.

Malpiedi L.P et al., "Studies of protein partition in non-conventional aqueous two-phase systems as method to purify trypsinogen and alpha-chymotrypsinogen from bovine pancreas", Separation and Purification Technology, vol. 78, Issue 1, Mar. 24, 2011, pp. 91-96.

Porfiri, M.C. et al. "Aspergillus oryzae alpha-amylase partition in potassium phosphate-polyethylene glycol aqueous two-phase systems", Int. J. Biol. Macromol., Jul. 1, 2011, vol. 49, No. 1, pp. 7-13.

Bassani, G. et al., „Porcine pancreatic lipase partition in potassium phosphate-polyethylene glycol aqueous two-phase systems, J Chromatogr B Analyt Technol Biomed Life Science, Nov. 15, 2007; vol. 859, No. 2, pp. 222-228.

Chaubal, M.V. et al. „Excipient selection and criteria for injectable dosage forms. In: Kathdare, A., Chaubal, M.V.: Excipient Development for Pharmaceutical, Biotechnology and Drug Delivery Systems. InformaHealthcare, New York, London 2006, pp. 271-290.

Gokarn, Y.R. et al., „Excipient for protein drug. In: Kathdare A., Chaubal M.V.: Excipient Development for Pharmaceutical, Biotechnology, and Drug Delivery Systems. InformaHealthcare, New York, London 2006, 291-331.

Scheuch, G. et al.," Deposition, Imaging, and Clearance: What Remains to be Done?", Journal Of Aerosol Medicine And Pulmonary Drug Delivery, vol. 23 No. 2 , Dec. 6, 2010, pp. 39-57.

Forbes, B. et al., Challenges in inhaled product development and opportunities for open innovation, Adv. Drug Deliv. Rev., vol. 63 No. 1-2, Jan.-Feb. 2011, pp. 69-87.

Patton, J.S. et al. "Inhaling medicines: delivering drugs to the body through the lungs ", Nat. Rev. Drug Discovery, vol. 6, Jan. 2007, pp. 67-74.

Balducci, A.G. et al., "Pure insulin highly respirable powders for inhalation", European Journal of Pharmaceutical Sciences, vol. 51, Jan. 23, 2013, pp. 110-117.

Chow, A.H.L. et al., "Particle Engineering for Pulmonary Drug Delivery", Pharmaceutical Research, vol. 24, No. 3, Mar. 2007, 411-437.

Mehnert, W et al. „Solid lipid nanoparticles Production, characterization and applications, Adv. Drug Deliv. Rev., vol. 47, No. 2-3, Apr. 2001, pp. 83-101.

Byrappa, K., et al. „Nanoparticles synthesis using supercritical fluid technology-towards biomedical applications, Adv. Drug Deliv. Rev., vol. 60, No. 3, Feb. 2008, pp. 299-327.

Huynh, G. H., et al. "Barriers to carrier mediated drug and gene delivery to brain tumors", J. Control Release, vol. 110 No. 2, Jan. 10, 2006, pp. 236-259.

Hearnden V. et al., "New developments and opportunities in oral mucosal drug delivery for local and systemic disease". Adv. Drug Deliv. Rev., vol. 64, No. 1, Jan. 2012, pp. 16-28.

Klein, S. et al., "Encapsulation of Bacterial Cells in Electrospun Microtubes", Biomacromolecules, vol. 10, No. 07, May 12, 2009, pp. 1751-1756.

J. W. Adelson et al. "Pancreatic digestive enzyme secretion in the rabbit: rapid cyclic variations in enzyme composition", Proceedings of the national academy of sciences, vol. 92, No. 7, Mar. 28, 1995, pp. 2553-2557.

Hansen L. J. et al."Immunohistochemical localization of pancreatic exocrine enzymes in normal and neoplastic pancreatic acinar epithelium of rat." Journal of Histochemistry & Cytochemistry, vol. 29, No. 309, Feb. 1981, pp. 309-313.

"Enzymova terapia a prevencia (NIE LEN) rakoviny," 18.7.12 www.badatel.sk/kpm/enymova-terapia-a-prevencia-nie-len-rakoviny/ (in CZ search report).

Avendano, C., Menendes J.C, Medicinal Chemistry of Anticancer Drugs. Elsevier, Amsterdam 2008, 431-442.

Bohe, H. et al., Immunohistochemical Demonstration of Pancreatic Secretory Trypsin Inhibitor in Normal and Neoplastic Colonic Mucosa, J. Clin. Pathol., 43,1990, 901-904.

Cancer Fighting Strategies, Enzymes for Cancer: Low Enzymes are Always Found in Cancer, Jun. 7, 2018, retrieved from the internet: www.cancerfightingstrategies.com/enzymes-for-cancer.html.

Currie, G.A., Bagshawe, K.D., The Masking of Antigens on Trophoblast and Cancer Cells, Lancet 279 (7492), 1967, 708-710.

Dhaneshwar et al., Dextran: A Promising Macromolecular Drug Carrier, Indian Journal of Pharmaceutical Sciences, 68(6), 2006, 705-714.

Glyceryl Trioleate from Olive Oil (Olive Oil Triolein), retrieved from the internet Jun. 8, 2018: www.alibaba.com/product-detail/GLYCERYL-TRIOLEATE-FROM-OLIVE-OIL_50017469779.html.

Homaei et al., Enzyme Immobilization: An Update, J. Chem. Biol., vol. 6, 2013, 185-205.

Jungo, C., Marison, I., von Stockar, U., Mixed Feeds of Glycerol and Methanol Can Improve the Performance of Pichia Pastoris Cultures: A Quantitative Study Based on Concentration Gradients in Transient Continuous Cultures, J. Biotechnol., 128(4), 2007, 824-837.

Lee, G.: Spray Drying of Proteins, in: Carpenter, J. Manning M. (Eds.), Rational Protein Formulation: Theory and Practice. Plenum Press, New York, 2002, 135-158.

Tan, Angel, Shasha Rao, and Clive A. Prestidge, Transforming Lipid-Based Oral Drug Delivery Systems into Solid Dosage Forms: An Overview of Solid Carriers, Physicochemical Properties, and Biopharmaceutical Performance. *Pharmaceutical Research* 30(12), 2013, 2993-3017.

Examination Report dated Jan. 28, 2020 from corresponding Indian Application No. 201637017157.

International Preliminary Report on Patentability dated Nov. 25, 2015 from corresponding PCT Application No. PCT/CZ2014/000133.

International Search Report and Written Opinion dated Apr. 16, 2015 from corresponding PCT Application No. PCT/CZ2014/000133.

Notice of Reasons for Rejection and English Translation dated Feb. 19, 2019 from corresponding Japanese Application No. 2016-553704.

Notice of Reasons for Rejection and English Translation dated Jun. 12, 2018 from corresponding Japanese Application No. 2016-553704.

Office Action dated Dec. 5, 2017 from corresponding European Application No. 14814733.3.

Office Action dated Feb. 25, 2014 from corresponding Czech Application No. PV 2013-891.

Office Action dated Dec. 6, 2018 from corresponding Eurasian Application No. 201691018 and English summary of relevant section.

Office Action dated May 25, 2018 from corresponding Eurasian Application No. 201691018 and English summary of relevant section.

Office Action dated Feb. 25, 2014 from corresponding Czech Application No. PV 2013-891 and English translation of relevant section.

Office Action dated Mar. 3, 2016 from corresponding Czech Application No. PV 2013-891 and English translation of relevant section.

Office Action dated Sep. 27, 2016 from corresponding Czech Application No. PV 2013-891 and English translation of relevant section.

Search Report dated Feb. 24, 2014 from corresponding Czech Application No. PV 2013-891.

PHARMACEUTICAL COMPOSITION CONTAINING A MIXTURE OF PROENZYMES AND ENZYMES

CROSS-REFERENCE TO RELATED APPLICATIONS

This application is a divisional Application of U.S. application Ser. No. 15/037,331, filed May 18, 2016, which is a National Phase Application of PCT International Application No. PCT/CZ2014/000133, International Filing Date Nov. 12, 2014, published as WO 2015/070828 on May 21, 2015, claiming priority of Czech Republic Patent Application No. PV 2013-891, filed Nov. 18, 2013, which are hereby incorporated by reference.

SEQUENCE LISTING INCORPORATION

The instant application contains a Sequence Listing which has been submitted electronically in ASCII format and is hereby incorporated by reference in its entirety. Said ASCII copy, created on Aug. 4, 2016, is named P-80155-US1-SEQ_ST25.txt and is 37,900 bytes in size.

TECHNICAL FIELD

The invention deals with new pharmaceutical compositions containing a mixture of proenzymes and enzymes having anti-proliferative and anti-metastatic effects.

BACKGROUND ART

Malignant neoplastic diseases represent a vast group of diseases that are one of the worst curable death causes. They cause 13 percent of deaths per year recently. (Jemal A. et al., CA: Cancer J. Clinic., 61, 2011, 69-90.). Occurrence of malignant tumors brings dangers given by the ability of tumor cells to change adjacent cells while new blood vessels, further supporting cells and metastases are produced.

Anti-neoplastic pharmacotherapy is an important part of large spectrum of present treatment approaches. In terms of therapeutic position pharmacotherapy of neoplastic diseases is divided to adjuvant (affecting so called residual disease e.g. after a surgical operation), non-adjuvant (preceding operation and radiation treatment, aimed at tumor devitalisation and inhibition) and metro therapy (long-term application of minimum doses of cytostatics affecting neoangiogenesis in advanced forms of neoplastic diseases.

Involved authorities like World Health Organisation WHO, Federal Drug Administration (FDA), European Medicines Agency (EMA) or State Institution for Drug Control (SUKL, Prague, CR) register more than 260 substances for oncology disease pharmacotherapy recently, classified by WHO (Collaborating Centre for Drug Statistics Methodology) according to application, therapeutic and chemical criteria into three main ATC subgroups: (http://www.whocc.no/; on line 25. 6. 2012): 1. Cytostatics (with 5 subgroups), 2. Hormonal medicines (2 subgroups), 3. Imunostimulants (4 subgroups) and 4. immunosuppressives (5 subgroups). About 160 substances of immunostimulant and immunosuppresive groups have FDA licence at present. With regard to ATC classification numerous details of anti-neoplastic substances and their mechanism activities can be found for example in current monograph Avendano, C. and Menendez, J. C., Medicinal Chemistry of Anticancer Drugs, Elsevier, Amsterdam, 2008, 431-442.

Antimetabolites, mitotic inhibitors, hormonal function inhibitors, reactive radical substances, photosensitizers, DNA alkylation agents, DNA separation spindle interactors, intercalators and topoisomerase inhibitors, tubulin and microtubules, attacking substances, inhibitors of cancer growth signals and proliferation are described there in the list of substances and mechanisms.

Classification based on cellular biologic mechanisms seems to be very interesting from theoretical point of view as well as for practical purposes. It fully respects the fact that mutual interaction between drug, tumor and its host is logically responsible for the final response to therapy (Wu, Xi-Z.: Medical Hypotheses 66, 2006, 883-887). From this viewpoint anti-neoplastic drugs are divided to cytotoxic substances and biological cell modifiers that kill tumor cells. They are often used as basic medicines. The other two groups, biological response modulators and biochemical modulators contain substances that are considered medicines used for adjuvant combined therapy.

Results of recent intensive research into mechanisms of effects of cytostatics and immunomodulation anti-neoplastic substances and progress in biopharmaceutical research have brought extremely wide spectre of findings but also new questions.

Now it is clear that normal cell growth, activity and functions are coordinated and regulated by a multilateral network of signal pathways that receive extracellular signal molecules and via a cascade of proteins and activation of gene transcription coordinate a wide scale of processes like growth, proliferation, invasion and apoptosis (Dowanward, J., Nature 411, 2001, 759-762). New strategies are aimed at protein-protein type interactions (Wells, J. A., McClendon, C. L., Nature 450, 2007, 1001-1009), which are undoubtedly also used in our new composition with enhanced role of tertiary structure of substances of this type both on pharmacodynamic parameters and particularly inherently pharmacokinetic parameters.

We can add in general that any intervention in such a complicated and still little known system always leads to some consequences, which are however not always known or predictable or positive. Drawbacks of present pharmacotherapy in oncology are also linked to them.

Disadvantages of Present Oncologic Pharmacotherapy

Human carcinomas occur as subsequence of various factors and their cells themselves further influence cellular signalling and paths regulating cellular proliferation and the time of survival of the other cells. Complex cellular signalling in a cancer cell is modified, the number of stimuli that tumors react to decreases, but the reaction intensity increases. This represents the base of increased sensitivity of tumors to genotoxic stresses and immune influences (O'Driscoll, L., Cur. Cancer Drug Targets 9, 2009, 250-251).

Cancer treatment success varies a lot today depending on particular malignity type. Some types of cancer diseases, e.g. testicular seminoma, infant leukaemia, and some lymfoms are very sensitive to anti-neoplastic treatment (Gonzalez-Angulo, A. M et al., Adv. Exp. Med. Biol., 608, 2007, 1-22). Other malignant cancer diseases show a limited response only (if any) and no efficient therapy is available against them now. (Jemal, A. et al., CA Cancer J. Clin., 60, 2010, 277-300). In the instances of advanced tumors with developed metastases, chemotherapy remains palliative treatment in better cases. If we define success rate of present pharmacotherapy by the survival time of cancer patients, we find that this essential parameter of treatment factually has nearly not changed for the last 30 years. Achieved success has actually to be attributed to timely diagnostics (Hemminki, K., Annals Oncol., 23, 2012, 760-764). Moreover, most of the clinically approved anti-neoplastic medicines are characterized by narrow therapeutic window, which is particularly related to their high systemic toxicity (Lowenthal, R. M.; Eaton, K., Hematol. Oncol. Clin. North Am., 10, 1996, 967-90).

Resistance against anti-neoplastic medicines represents another serious problem, particularly in long-term treatment (Redmond, K. M. et al.: Front. Biosci., 13, 2008, 5138-5154), whether based internally in tumor cells (intrinsic resistivity) or it is acquired. Multiple resistance against higher number of anti-neoplastic substances, often of different structures and functions, appears more and more often (Wu, Ch.-P. et al.; Curr. Pharm. Biotechnol., 12, 2011, 609-620). This clinical resistance is multifactorial and heterogeneous with numerous molecular mechanisms. (Glickman, M. S., Sawyers, C., Cell 148, 2012, 1089-98). Relatively short history of targeted biological cancer treatment has already been filled with wide spectrum of resistances (Gorre, M. E. et al., Science 293, 2001, 876-880).

Probably the most critical aspects of oncologic pharmacotherapy are linked to higher risk of unwanted induction of immunogenic responses or toxic effects as most of the newer medicines belonging to groups ATC 3 and ATC 4 are supramolecular active substances mainly of biotechnological origin. They belong to so called biopharmaceuticals, today biologics, protein therapeuticals, and each of them has actually a potential to affect hundreds of physiological processes in a patient (Yang, J. A.; Hastings Sci. Tech. L. J., 3, 2011, 217, 1-18), which represents substantial growth compared to medicines with small molecule. The risks of immune responses include hypersensitiveness, anaphylaxis, pseudoallergic anaphylactoid reaction, series disease, reaction to infusion, therapeutic effect reduction (Borges, S. et al., Clin. Pharmacol. Ther. 74, 2006, 61-74; Barbosa, M. D. F. S., Drug Disc. Today 16, 2011, 345-53), generation of antibodies against the medicine and cross reaction between antibodies for therapeutic and endogenous proteins (Wager K., Jones, G.: Cur. Biotechnol., 297, 2012, 297-317). This certainly brings extended demands for production conditions (Singh, S. K., J. Pharm. Sci., 100, 2011, 354-87), including control mechanisms, which affects the price of the medicines. This is also the reason why these medicines are often used not only monotherapeutically, but also in combinations with conventional chemotherapeutics, sequentially and in link to further physical and/or surgical methods.

The fact that in 98 percent of cases it is only linked to parenteral injection or infusion administration is another disadvantage of present pharmacology of tumors by substances of biologics group. This means that parenteral administration approach and related medicine forms are elaborated in detail. On the other hand, all principal disadvantages of parenteral administration itself remain unsolved, from higher risk of infection in the needle mark to patient non-compliance even in the link to the hospital and its qualified staff. Vast majority of biologics have only a short plasma half-life and has to be applied by infusion.

The above reference to the existing disadvantages of oncologic pharmacotherapy means in general that alternative conceptual and practical approaches to anti-neoplastic disease treatment are still required (Sachlos, E., et al., Cell 149, 2012, 1284-1297), and that the existing range of anti-neoplastic substances has to be extended by medicines that do not have the above briefly summarized disadvantages or are at least able to reduce them.

DISCLOSURE OF THE INVENTION

The solution is based on a pharmaceutical composition containing a mixture of proenzymes and enzymes, containing proenzymes trypsinogen and chymotrypsinogen and enzymes α-amylase and lipase as active substances, and one or more pharmaceutically acceptable excipients, for simultaneous, separate and subsequent administration of the composition in parenteral or transmucosal way, while the composition has anti-proliferative and anti-metastatic effects to cancer tumors and is intended for therapeutic, prophylactic and anti-metastatic use in mammals.

The pharmaceutical composition has advantageous ratio of enzymatic active substances, namely activities of trypsinogen (T), chymotrypsinogen A (CH), α-amylase B.s (A) and lipase T.a. (L) for T:CH:A:L ratio expressed in international units ("i.u.") in the range from 150:150:40:1 to 400:1200:200:1

The above pharmaceutical composition advantageously contains trypsinogen of type I, chymotrypsinogen of type A, α-amylase is produced by *Bacillus* sp. and lipase is from *Triticum aestivum*.

The minimum enzymatic activity of active substances in the pharmaceutical composition according to the invention is advantageously as follows: trypsinogen 40 i.u./mg, chymotrypsinogen 60 i.u./mg, α-amylase 20 i.u./mg and lipase 1 i.u./mg.

At least one of the active substances in the pharmaceutical composition according to the invention is advantageously replaced with biologically similar substance obtained by extraction from higher plants, animals or by cultivation procedures using mold cells, yeast cells, or bacteria, the primary structure of the biologically similar substance with the active substance which it has replaced in the composition being at least 70% identical and the position of active places essential for the effect is at least in 95% identical.

The pharmaceutical composition according to the invention is particularly suitable for systemic sublingual, rectal, inhalation or parenteral administration.

The pharmaceutical composition according to the invention may contain numerous substances as pharmaceutically acceptable excipients, particularly one or more hydrophilic polyhydric alcohols including polyethylene glycol with mol. weight 100 to 8000 and/or hydrophilic low molecular alcohols like glycerol, propylene glycol, n-propanol, and/or saccharides like trehalose, mannitol, lactose, sorbitol, myo-inositol, and/or polysorbates like polysorbate 20, polysorbate 60, polysorbate 80, poloxamers like poloxamer 182, poloxamer 417, poloxamer 908, and/or one or more lipophilic excipients including hydrogenated triglycerides like hydrogenated glycerol trioleate, hydrogenated glycerol-cocoate, and/or esters of higher fatty acids with glycerol or propylene glycol like glycerol-tripalmitate, glycerol-trioleate, glycerol-tristearate, glycerol-distearate, glycerol-dioleate, glycerol-monolaurate, propylene glycol-myristate, glycerol-dipalmitostearate, and/or esters of lower monovalent alcohols like diisopropyl-adipate, isopropyl-laurate, isopropyl-linoleate, isopropyl-palmitate, and/or esters of higher fatty acids with medium and higher fatty alcohols, including myristyl-strearate, capryl-stearate, cetyl palmitate, caprin-behenate, lauroyl oleate, and/or higher fatty alcohols, including lauryl alcohol, myristyl alcohol, palmityl alcohol, stearyl alcohol, behenyl alcohol and analogously higher fatty acids like lauric, myristic, palmitic, stearic, lignoceric, arachidonic, behenic acids and their ethoxylated derivatives like polyethylene glycol 10 oleyl alcohol, polyethylene glycol 25 stearyl alcohol, polyethylene glycol 40 stearyl alcohol, stearoyl polyethylene glycol 32 glycerol, polyethylene glycol 15 hydroxy stearate, and/or vegetable oils, including cottonseed oil, sunflower oil, groundnut oil, soya oil, castor oil, and their ethoxylated derivatives like polyoxyl 35 ricinoleate, and/or phospholipids including egg lecithin, soya lecithin, dioleoylphosphatidylcholine, dipalmitoylphosphatidylserine, and/or sterols including cholesterol and its derivatives like cholesteryl-linoleate, cholesteryl-acetate, and/or biocompatible and biodegradable polymers particularly polyesters like poly-DL-lactic acid (PDLLA), polyglycolic acid (PGA), poly-DL-lactic glycolic acid (PLGA).

If the pharmaceutical composition is designed for sublingual administration, it is advantageously in the form of nanofibers, while it contains at least one of polyvinyl polymers like polyvinylpyrrolidone with molecular weight approx. 30,000 to 50,000 and polyvinyl alcohols with molecular weight from 20,000 to 200,000, of cellulose derivatives like methylcellulose, hydroxypropyl methylcellulose, hydroxypropyl cellulose and/or polysaccharides of starch type like hydroxyethyl starch, carboxymethyl starch sodium salt and/or dextrins with molecular weight from 4,000 to 80,000 and/or of biotechnological polysaccharides of dextran type with molecular weight from 10,000 to 80,000, and/or glucuronate type substances like xanthan mucilage, and/or further polyuronides especially their salts, particularly sodium, potassium, like hyaluronans, alginans, pectinans, arabinans and/or polymers based on acrylic, methacrylic acids and/or their copolymers like carboxyvinyl polymers (carbomers) netted with spolyalkenyl ethers of sugars or poly alcohols (like diallyl sucrose a diallylpentaerythritol, biodegradable polyesters of α-hydroxy acids like (PDLLA), (PGA), (PLGA), polycaprolactones with molecule weight from 10,000 to 100,000, further polymeric excipients of copolymer type like polyvinyl caprolactam-polyvinyl acetate polyethylene glycol.

If the pharmaceutical composition or its part is designed for inhalation administration it advantageously also contains at least one or more saccharides, including trehalose, mannitol, glucose and/or various forms of lactose.

The pharmaceutical composition according to any of the claims may advantageously be in the form of nanofiber stabilized preparation for direct administration of active substances or as stabilized storage of active substances in an intermediate product or in the final preparation.

It is a composition of proenzymes and enzymes representing a substantial modification of enzyme therapy by its composition and efficiency. It solves the main side effects of present oncologic treatment based particularly on impact on lively divided healthy tissues like gastrointestinal system mucous membrane, medulla, liver and kidney parenchyma. This is thus targeted biological therapy in the real sense of the word, non-toxic, selectively focused on tumor cells, wide spectral from the point of view of anti-neoplastic effects. It impacts on carcinomas, sarcomas, as well as acute haematological malignity.

Dosage of the therapeutic composition is only limited by the minimum daily dose in relation to the volume of degrading elements originating from tumor cells. Due to the intrinsic non-toxicity of the composition according to the invention, where particularly, or only degrading products from decomposed tumor cells may have toxic effect, the composition may also be used for diagnostic purposes and actually with regard to the experience gained from application of in vivo methods of testing the efficiency on lines of tumor cells grown on mice it is obvious that the composition according to this application will have anti-neoplastic effect not only in humans, but its effect against tumors affecting animals, e.g. a dog or a cat may also be anticipated. However, their different anatomy as well as immunogenicity has to be taken into account, while such influences can hardly be predicted.

The minimum daily dose means such a quantity of the anti-neoplastic composition that ensures full or partial therapy of a tumor diseases or the required diagnostic or prophylactic effect with regard to the current state of the tumor disease and in relation to the chosen administration method.

Stabilization of the individual components of the anti-neoplastic four-composition according to this application is solved for the purpose of elaboration into a pharmaceutical preparation and for the administration purposes by means of excipients and procedures ensuring preservation and actually regeneration of the secondary and higher supramolecular structures of the partial active components.

Systemic administration in non-invasive ways, which may be advantageously applied to the anti-neoplastic composition according to the invention solves one of the current important problems of biologic medicine administration (biologics, protein therapeutics etc.), which is the short plasmatic half-time of these substances in organism.

DETAILED DISCLOSURE OF THE INVENTION

The new solution according to the invention is fundamental, empirically observed from influences on trophoblast as a biologic model of malignant tumors even at the molecular level (Soundarajan, R., Rao, J., Reprod. Biol. Endocrinol., 2, 2004, 15. The solution is based on classic concept of J. Beard (Beard, J.: Lancet 168, 1905, 281-283), who proposed treatment of advanced carcinomas by fresh pancreatic extracts. Their anti-tumoral activity was based on proteolytic potential. He assumed that enzymes produced by pancreas limit trophoblastic invasion and he concluded that pancreatic extracts should have similar inhibition effects to invasive tumors. In the following years extract from pancreatic enzymes were thoroughly examined for that time. It was found that they really very efficiently inhibit cancer growth even in patients at advanced stage of malignant neoplasm (Goeth, R. A., J. Am. Med. Assoc. 1907; 1030). With regard to several subsequent reports on negative effects of administration of then very imperfectly processed pancreatic extracts the research was abandoned for a long period (Gurchot, Ch., Oncology 31, 1975, 310-333). Later traceable exceptions from recent years (e.g. Maeda et al.: EU Pat. 0215 662 A2, 1986) only mention proteases, not protease proenzymes, zymogens.

The hypothesis that proenzymes and not activated enzymes are the crucial components of extract effects was first formulated and then elaborated in detail by F. Trnka (Trnka, F. et al.: EU Pat. 0743 070 A2, 1996; CZ Pat. 283 972, 1998; U.S. Pat. No. 5,858,357; 1999). About thirty years ago this author discovered and experimentally confirmed the fact that a mixture of trypsinogen, chymotrypsinogen and amylase, approximately in the concentrations proposed by J. Beard, has strong anti-tumoral, anti-invasive and anti-angiogenic effect. One of the effects of the above proenzymes and their mixture with amylase is inhibition of tumor cells migration at the cellular level. F. Trnka et al. also discovered (Novak, J., Trnka, F.: Anticancer Res., 25, 2005, 1157-77) that continuous exposition of tumor cells to low concentration of the above substances leads to formation of cell aggregates and inhibition of metastases. He managed to combine the historic data with new findings and he deduced that (a) protease proenzymes are resistant to inactivation of protease inhibitors,
(b) proenzyme activation only occurs in tumoral cell membrane,
(c) active serine proteases destroy cell surface of tumoral cells, they have apoptotic effect, which are the substantial findings on which this invention is based.

One of the characteristics of the invention is thus yet not described integration of lipase enzyme into anti-neoplastic composition and its wide-spectral efficiency newly distributed and confirmed by us.

Effect of Mixture of Protease Proenzymes and Hydrolytic Enzymes

The importance of in vivo application of protease proenzymes instead of active proteases is based on the existence of plasma anti-proteases, which together with proteases form complexes that prevent protease penetration to tumoral cell surface (Currie, G. A., Bagshawe, K. D., Lancet 279 (7492), 1967, 708-10). These anti-proteases are particularly alpha-1 antitrypsin and alpha-2 macroglobulin (Lah, T. T. et al., Expert Opin. Biol. Ther., 6, 2006, 257-279), for which proenzymes are illegible. The anti-tumoral selective effect of proenzymes of pancreatic proteases is based on presence of pancreatic secretory inhibitor (PSTI) formed by pancreatic acinar cells, which protect it against autodigestion. This inhibitor was also found on the surfaces of mucous membrane cells of stomach, small and large intestines, on adenoma cells, but not on carcinoma cells (Bohe, H. et al., J. Clin. Pathol., 43, 1990, 901-904).

Nonparticipation in hemocoagulation cascade and invasive character of malignant tumors is another advantage of proenzyme application. Due to trypsin activity of malignant tumors protease proenzymes are selectively activated on tumor cells. This property of proenzymes circumventing the anti-protease protective effect does not affect tumor cells in vitro, where it is unimportant whether active proteases or their proenzymes are used. By in vitro trials we have demonstrated aggregative impact on tumor cells and by further in vivo trials also inhibitive impact on tumoral proliferation and metastases in several crucial lines of human tumor cells.

Finding that cells that did not respond succumbed to apoptosis was important (Trnka F. et al., EU Pat. 0743 070 A2, 1996; Novak, J. F., Trnka, F., Chernin, M. I., AACR Meeting Abstracts, April 2006; 1023-1024.) Further authors described the suppressive role of trypsin to tumor progression by epigenetic mechanism (Yamashita, K. et al., Cancer Res., 63, 2003, 6575-6578), or anti-proliferative effects of strong alpha-amylase to mouse or human cancer cells by mediation of cellular adhesion and stimulation of cellular anoikis of apoptosis type (Fedrowitz, M. et al., J. Exp. Clin. Cancer Res., 30, 2011, 102-114). Elevation of plasmatic level of endostatin and angiostatin, and thus limitation of vascular neoplasm was also proven.

Amylase effect on tumor cells is thus being studied again as well as the role of trypsinogen and chymotrypsinogen (Itkonen, O., Scandin. J. Clin. Lab. Invest., 70, 2010, 136-143; Koskensalo, S. et al.: Oncology 82, 2012, 234-241) and effect of lipases (Nomura, D. K. et al., Cell 140, 2010, 49-61), namely triacylglycerol hydrolases, EC 3.1.1.3 as serine proteases, whose combined use is the principle of the effect of the four-composition according to this invention application.

The anti-metastatic effect of the therapeutic, diagnostic and prophylactic composition according to the invention is newly extended and boosted compared to the above state of the art by addition of vegetable lipase (Aub, J. C, Tieslau, C., Natl. Acad. Sci. USA, 50, 1963, 613-619), characterized at the active point by a triad of histidine-asparagine amino acids.

Therapeutic effect was demonstrated in nu/nu mice both in subcutaneous and rectal administration of the preparation in standardized trials with subcutaneously transplanted lines of human cells of mammary carcinoma, colorectal carcinoma, pancreatic carcinoma, and small-cell lung carcinoma.

Today, we assign the universal anti-tumoral effect of the composition regardless of the origin of the affected tumors to the presence of sialized molecule of glycoprotein choriogonadotropin (Currie, G. A., Bagshawe, K. D., Brit. J. Cancer 22, 1968, 848-853; Willey, K. P. et al., J. Biol. Chem., 264, (1989), 1971, 619-729; Acevedo H. F. et al., Cancer 69, 1992, 1818-1928; Acevedo H. F. et al., Cancer 78, 1996, 2388-99), which we consider to be the target structure for chymotrypsinogen (Regelson W., Cancer 76, 1995, 1299-1301; Illes R. K.: Mol. Cell. Endocrinol., 260-262, 2007, 264-270) and amylase (Varki, N. M., Varki, A., Lab. Invest. 87, 2007, 851-857). This sialized centre is probably the carrier or mediator of the invasive and metastatic properties of malignant tumors (Nguyen, D. H., Tangvoranuntakul, P., Varki, A., J. Immunol., 2005; 175, 228-236).

Innovative application of lipase has been backed by recent finding of D. K. Nomura et al. who demonstrated experimentally that monoacylglycerol lipase (MAGL) regulates creation of free fatty acids in cancer cells, which enables them to create oncogenic lipidic signalling that increases migration, invasiveness of tumoral cells, tumor growth and pathogenicity. They found by means of proteomic approach based on analysis of tens of superordinate serine hydrolases that the MAGL levels are permanently increased right in the cells of aggressive tumors and they probably also pass aggressiveness to non-aggressive cells (Nomura, D. K., Long, J. Z., Niessen, S., et al., Cell 140, 2010, 49-61).

The wide-spectral anti-neoplastic effect of the new composition is given by its new structure, which accepts the complex relations in living organism of humans or animals. It does not prevent occurrence of tumor cells, however it destroys tumor cells that have already appeared, which restores and maintains complex balances of biological environment in normal healthy condition, limits occurrence and propagation of oncogenic signals.

Displays of the therapy based on anti-neoplastic composition administration like perspiration, breathing, urination and excrements of specific smell are also interesting and practically applicable. It is moreover accompanied by exhaustion, even somnolence or pains in muscles. All these signs are important, subjectively and clinically readable displays of the medicine contact with tissue affected by tumor. They actually do not indicate toxicity of the preparation as such but toxicity of products resulting from its impact on tumor cells. In this sense these signs also represent an important indicator whether tumor tissue is present in the organism or not. Unless any of the above signs occur after two or three days of administration of usual initial therapeutic doses of the composition according to the application there is very high degree of certainty that tumor cells are not present in the individual. In other words, with minimum toxicity, the composition according to the invention may be used in the above sense for diagnostics of tumor disease in asymptomatic period in individuals who have not noticed any disease symptoms yet.

In this relation we should mention the possibility of the use of hemodialysis or actually hemoperfusion, which may be applied if necessary in administration of such doses of the composition according to the invention that might threaten important life function of the patient as a subsequence of tumor cells destruction. Such an approach certainly requires specialist guidance and supervision of a clinical oncologist.

The principle of prophylactic utilization of the anti-neoplastic composition according to the invention may be basically described analogically. With regard to the minimum own toxicity of the preparation a period of administration of therapeutic doses of the composition may be included in the process of patient oncology monitoring. If tumor cells and thus the substrate for the activity of the preparation components were present in the organism the preparation administration would in fact already provide its effect prophylactically with the above accompanying symptoms.

The combined diagnostic and prophylactic effect of short-term administration of the composition thus also appears in an individual in whom no signs of oncology disease have occurred yet. Unless any of the above described symptoms occurs after preparation administration this fact can be logically considered an indicative proof of oncologic health.

The solution according to the invention is based on composition of two proenzymes of trypsinogen and chymotrypsinogen group with alpha-amylase and lipase (hereinafter also collectively referred to as active substances) defined from activity point of view. This four-composition shows in in vivo conditions surprisingly substantial positive effects towards wide spectre of tumor cells of completely different histological characteristics, as mentioned above, both after injection subcutaneous administration and non-invasive transmucosal, particularly rectal administration.

Partial Components of the Anti-Neoplastic Composition

The composition according to the invention represents a combination of enzymes and proenzymes obtained by extraction from organs (tissues) of animals (particularly mammals), plants and/or substances produced by cultivation methods using molds and microorganisms or e.g. by continuous perfusion of mammal cells and consequent supernatant processing. With improvement of separation and analysis methods the proportion of cultivation process products is growing.

At today's level of knowledge in the field of biotechnology it is practically possible to obtain the appropriate proenzymes (Jungo, C., Marison, I., von Stockar, U.; J., Biotechnol., 128, 2007, 824-837; Paulova, L. et al., J. Biotechnol., 157, 2012, 180-188) and both the appropriate enzymes, i.e. all the necessary active substances of the composition by both the basic approaches.

Production procedures usually lead to production of isolated proteins and polypeptides, which are carefully taken from their natural environment, separated and identified. Contaminants originating from natural material may affect therapeutic, diagnostic and prophylactic use of proteins and polypeptides. They may contain not only protein components, but also numerous contaminants of various characters. They may lead to change of the original natural protein composition particularly to its glycosylation, secondary change or change of higher supramolecular structures, which might lead to undesirable immune or other reactions when administered to living organism. It is considered proven nowadays that not only the primary structure of proteins decides on their final interactions in organism, but obviously particularly the secondary and tertiary structures of proteins, which are in direct physical and chemical interactions with biological environment.

Because of the fact that any small changes of conditions may cause undesirable results mainly in cultivation procedures, very detailed and costly control of production processes, but also quality of final products is necessary. We know that this is also why the price of biologics is in average more than twenty times higher than the costs of medicines obtained by methods of conventional low-molecule chemistry or extraction and purification processes from organs and tissues of commonly accessible animals and plants.

It is thus necessary to define not only their original primary, secondary and tertiary structures, but for their further use also the acceptable deviations from the models of proteins and polypeptides in their original natural state. This is why not only requirements for purity are defined, e.g. 95% or preferably even 99% (depending also on chosen purity assessment method), acceptable residuum quantities, e.g. on N-terminal termination of the protein of protein amino acid internal sequence or amino acid chain glycosylation, but also acceptable percentage difference of the structure of those parts of protein or polypeptide that are important for the effect.

On the other hand we should stress that it has already been proven that changes in enzyme primary structure, e.g. in serine proteases do not have to lead to a change of enzyme function if the supramolecular structure of enzyme active part is preserved (Kraut, J., Annu. Rev. Biochem., 46, 1977, 331-58).

Next, but as well important fact is, that even primary amino acid sequence although it is authentic with the human protein model, does not guarantee immunocompatibility, as proven e.g. for erythropoietin (Prabhakar, S. S., Muhlfelder, T., Clin. Nephrology 47, 1997, 331-335) or interferon-$\alpha$2B (Oberg, K. et al., J. Natl. Cancer Inst. 81, 1989, 531-535).

Important consequences for intended use of enzymes follow from the above facts. It is generally accepted that in most cases of enzyme distribution in system circulation and their behaviour in organism are controlled by combination of their size, charge, position and inclusion of hydrophilic surface functional groups. Information exists how these properties affect link to proteins, behaviour in circulation, interaction with vascular endothelial cells, extravasal capillary beds, on distribution by means of tissue stroma and final communication with target cells. However unifying principles describing what is the best for protein medicine particles, particularly in living organisms under in vivo conditions, do not exist yet. From this point of view the structures for targeted creation of pharmaceuticals are still too complex and the existing knowledge of their interaction mechanisms is still insufficient.

Even in the context of tumor diseases we should always remember that activity of enzymes as well as proenzymes expressed upon arbitrarily defined methods does not have to correspond to anti-tumor activity of the individual active substances.

It is definitely necessary to define biologic products, proenzymes and enzymes correctly and reproducibly. This is why definition of the composition according to the invention is not based on weight, but on enzymatic activity units.

Importance of this approach is obvious e.g. from comparison of two commercially available proenzymes from two different suppliers: chymotrypsinogen with declared activity >40 i.u./mg vs. chymotrypsinogen A with activity=1,422.3 i.u./mg. This is why the requirement for definition of biologic activity is so crucial for usability of information on biological pharmaceutical composition, e.g. in the form of activity per weight unit (usually milligram) per given volume or per one dose. This way of stating enzymatic activity is still used even by renowned manufacturers although in the world of science expression of enzymatic activity in catals (cat) as units derived from the SI system has been considered correct for a long time (1 U: 60=μcatal; 0.01667 U=μcatal and 60 μcatal=U).

An important difference between the composition according to the invention and earlier patents by Trnka, F. et al. or Psaledakis N. G. (Psaledakis N. G: U.S. Pat. No. 4,514,388, 1985), also inspired by J. Beard's findings is also based on this aspect. This difference is also essential in comparison with analogous patents or patent applications by Kenyon, J. N. et al. based on the same idea which is therein hidden by heterogenic declaration of further claims related to various antioxidants and further potentially cancerostatic substances of heterogenic character. (Kenyon J. N. et al., Austral. Pat Appl. 2010310887, 2012; U.S. patent application Ser. No. 13/502,917, 2012; EP 2490711 A1, 2012). Moreover definition of the composition of the enzymatic preparations the last two mentioned patents refer to cannot in fact be based on weight of its substances, but on their enzymatic activity.

Production procedures for substances of the composition according to the invention including usual final lyophilization or spray drying use technology knowledge now well described and available in extensive scientific and patent literature. They not only enable obtaining high purity non-immunogenic products, but also products that may be modified unlike their natural models. Some of these modifications are aimed at improvement of some properties of their models, mostly stability properties or pharmacokinetic parameters. The other side of this progress and recently even a problem is the fact that routine production of modification of proteins, enzymes and polypeptides serves to circumvention of existing patent protection of the original substances, their compositions and preparations or actually abuse of the so called biosimilars way. The competent legislation authorities are trying to find and they gradually find consensus in this field in cooperation with scientific community. Data necessary for characterization of biological medicines, and also protein therapeutics have been gradually formulated for biosimilars in EMA directives. It is noted that the approach of the two regulatory authorities is somehow different, wherein the FDA is more reserved.

It is thus necessary to point out that each proenzyme (zymogene) and enzyme of our proposed anti-neoplastic composition may be obtained in tens of different was nowadays, some of which will naturally have the same effect as the substance used and tested by us and some will have not. Experts in the appropriate disciplines know that tens of substances belonging to the same enzyme classification group according to EC number have different primary structures, i.e. different numbers and orders of amino acids in chains, different numbers and positions of disulphide bridges, hydrophobic and hydrophilic parts of different lengths and locations, different places for substitution, different particular substituents, e.g. different sugar units glycosidically bound at different places and thus for example different behaviour in water environment, behaviour on interfaces, they may have different positions of active places for reaction with substrate. All that is given by the origin and by the method of production of the individual zymogens and enzymes.

Data and characteristics from scientific databases NCBI (http://www.ncbi.nlm.nih.gov/protein, on line 30.4.2013); and PDB http://www.rcsb.org/pdb/home/home.do, on line 30.4.2013) were used for specification of definition of proenzymes and enzymes of the anti-neoplastic composition according to this patent application.

The individual substances of the anti-neoplastic composition can be described by these characteristics and the extent of similarity of possible variations within that the same effects of both the partial components and the anti-neoplastic composition as a whole can be subsequently defined.

We thus consider important for the composition according to the invention that similarity of the particular variants of zymogens and enzymes therein used is roughly qualitatively specified by sequences of amino acids of the four tested substances (see Examples 2.1, 3.1., 4.1 and 5.1). In terms of the effect we should consider similar substances with at least 70% (and higher) correspondence of active places and sections of primary structures for the individual components of the four-composition, i.e. 70% correspondence for trypsinogen type I from bovine pancreas, for trypsinogen A from bovine pancreas, for α-amylase produced by *Bacillus* sp., and the same 70% correspondence for lipase from *Tritici aestivum*.

It is still true that no matter how important the enzyme amino acid sequence and its primary structure are, the enzyme participates in the effect itself in its supramolecular structure with particular positions of active places. The other parts of the enzyme are important in given context for its pharmacokinetics.

Necessary stabilization of the anti-neoplastic composition for the purpose of its elaboration into the pharmaceutical preparation is based on stabilization of the individual components. These components have to be assessed and evaluated as non-immunogenic for processing to the usable preparation and its administration. Their stabilization for processing and application is solved by using excipients and procedures that from the point of view of the present state of technology ensure preservation (or regeneration) of secondary and higher supramolecular structures of the partial active components and thus the four-composition according to our application as a whole (Lee, G.: Spray drying of proteins, in: Carpenter, J. Manning M. (Eds.), Rational Protein Formulation: Theory and Practice. Plenum Press, New York, 2002, 135-158). This is particularly application of procedures of processing solutions or dispersions of proteins by lyophilisation, spray lyophilisation, supercritical drying, possibly combination of dialysis and spray drying or cryogenic dispergation methods. If necessary, these methods are combined with application of a preparation from structurally stabilizing substances, particularly saccharides, e.g. sorbitol, trehalose, sucrose (Maury, M. et al., Eur. J. Pharm. Biopharm., 59, 2005, 251-261), polymers, e.g. polyethylene glycols, polyvinylpyrrolidones, dextrans, lipids, e.g. medium-chain triglycerides (Hauss, D. J., Adv. Drug Deliv. Rev.; 59, 2007, 667-76; Tan, A., Rao, S., Prestidge, C. A.; Pharm. Res., 2013, 2993-3017), selected surfactants e.g. dipalmitoylphosphatidylcholine, polysorbates, polyoxyethylene stearates (Mansour, H. M., Damodaran, S., Zografi, G.: Mol. Pharm., 5, 2008, 681-695), cryoprotectants, e.g. glycerol, ethylene glycol, propylene glycol, dimethyl sulfoxide; hydroxyethyl starch, polyvinylpyrrolidone (Meryman H. T.; Cryobiology 8, 1971, 173-183).

Mixture of polyethylene glycols (PEGs) of adequate purity e.g. stabilizes the active substances physically-chemically and is also suitable for processing the active substances into application structures both for non-invasive administration types and parenteral administration. Stabilization effects of glycerol and n-propanol have been similarly described and are usable. The solution of the anti-neoplastic mixture according to the invention in given context thus uses information published on purification, regeneration a stabilization of supramolecular structures, namely for all partial components of the composition according to the invention (Pellegrini-Malpiedi, L., Picó, G. A, Nerli, B. B., Separ. Purif. Technol., 78, 2011, 91-96; Porfiri, M. C. et al.: Int. J. Biol. Macromol., 49, 2011, 7-13; Bassani, G. et al.; J. Chromatogr. B, 859, 2007, 222-228).

Administration Methods and Ways of Application

There is a known and generally acceptable fact that oral administration of polypeptide therapeutics and proteins to living organism of a human or animal body through the gastrointestinal tract represents a basic problem that has not been even partially solved yet. The conditions in stomach or intestines might actually completely destroy such medicine or prevent its absorption in the active form. This is why parenteral application is dominantly used nowadays for administration of biologics or therapeutic proteins, to which the composition according to the invention belongs.

Composition of the mixture and its dosage may be modified in details according to chosen application way and consequently also according to the vehicle used for the particular active substance, and dosage in clinical conditions may be defined and optimized according to the current state of the tumor disease or according to organism response to administered dose. The anti-neoplastic composition according to the invention basically enables outpatient treatment approach. It moreover enables self-administration particularly when non-invasive administration methods are used, and use of corresponding preparation types e.g. for sublingual or rectal administration. We consider both these ways advantageous for administration of the composition according to the invention as well as inhalation method through lung alveolar walls. Good tolerance to the preparation and absence of allergic symptoms or other negative immunological or other biological responses of the patient are certainly the basic conditions.

Parenteral administration with all its alternatives brought by the latest technological development in this field may obviously be applied to administration of the anti-neoplastic composition according to the invention. Dry injections, including lyophilized, i.e. mixtures of pulverized forms of active substances and auxiliary substances modifying pH, osmolarity, wettability, solubility, antioxidant protection, in the case of lyophilized products also excipients of cryoprotectant type (glycerol, dimethyl sulfoxide), lyoprotectants and structural substances. These preparations are dispersed in suitable liquid vehicle at the time of use and administered by injection needle.

Injection preparations with prolonged or otherwise modified active substance release, which release the active substance slowly and for longer period after administration, where it is desirable, e.g. in intraperitoneal application may also be used. Further excipients, of which both slowly degraded lipids and biodegradable polymeric systems based on proven polymers or oligomers of glycol acid, lactic acid and their co-polymers (Chaubal, M. V. et al.: Excipient selection and criteria for injectable dosage forms. In: Kathdare, A., Chaubal, M. V.: Excipient Development for Pharmaceutical, Biotechnology and Drug Delivery Systems. InformaHealthcare, New York, London 2006, 271-290; Gokarn, Y. R. et al, Excipient for protein drug. 291-331. In: Kathdare A., Chaubal M. V.: Excipient Development for Pharmaceutical, Biotechnology, and Drug Delivery Systems. InformaHealthcare, New York, London 2006, 291-331) are used for depot administration.

Administration though alveolar epithelium, which is the most penetrable and in terms of useful area of the alveoli absolutely the largest mucosal surface, should be the most suitable from this point of view. Inhaled low molecular medicine may appear in system circulation in seconds, which is very close to intravenous administration. This trait of inhalation application is however not important for the composition according to the invention. The effect start time in seconds or minutes is not important in this case, and for macromolecular substances it is unachievable. The second, but more important factor in this relation is the fact that penetration of inhaled particles through the complicated tree of branching bronchi and bronchioles up to the alveolar surface has already been satisfactorily solved. Newer findings show that unlike in bronchodilatation and antiasthmatic drugs the optimum size of solid particles for systemic administration of dry pulverized medicines of protein type is somehow lower, namely 2 to 4 micrometers (Patton, J. S., Byron, P. R., Nat. Rev. Drug Discovery 6, 2007, 67-74). This requirement may already be technologically met nowadays. The issue is thus passed to technical sphere of particle engineering and inhalator technical solution. The backward movement of particles from the alveoli (Scheuch, G. et al., J. Aerosol Med. Pulm. Drug Deliv., 23(S2), 2010, 39-5; Forbes, B. et al., Adv. Drug Deliv. Rev., 63, 2011, 69-87). However, physiologically desirable, remains to be solved from biopharmaceutical point of view. This is probably apart from commercial reasons one of the causes of insufficiently reproducible inhalation administration of insulin in the past, which has already been solved by inhalator innovation and immediately also by carrier free modification of insulin (Balduci, A. G. et al., Eur. J. Pharm. Sci., 2013, http://dx.doi.org/10.1016/j.ejps.2013.08.009, on line 18 September 2013).

The composition according to the invention meets requirements for processability into the inhalation powder form both without further excipients and with suitable carrier (e.g. trehalose, lactose, mannitol), polyethylene glycol type substance of lower and medium molecule weight (e.g. macrogol 300 or macrogol 1500) and their mixtures. Inhalation of water dispersion of the composition according to the invention prepared at the time of application using nebulisers (e.g. electric or ultrasound) from ex tempore prepared water dispersions with the content of the above excipients, but also dextrans and suitable tensides (e.g. polysorbates) might have the same effect. The composition according to the invention is also suitable for processing into lipid micro particles, where their stabilizing and handling advantages and particularly advantageous properties as application systems for protein inhalation administration (Chow, A. H. L. et al., Pharm. Res. 24, 2007, 411-437; Mehnert, W., Mäder, K.: Adv. Drug Deliv. Rev. 64, 2012, 83-101) may become useful.

As various practically applicable methods of application of inhalation (transalveolar) administration of the composition according to the invention exist from the point of view of possible technologies for production of particles suitable for inhalation from the point of view of physics and stability, we present one of them adopted from literature (Byrappa, K., Ohara, S. Adschiri, T., Adv. Drug Deliv. Rev., 60, 2008, 299-327), in Example 12 of embodiment of cryogenic procedure of creation of particles of anti-tumor composition for inhalation.

Analogous statement also applies to formulation-technological aspect of the individual partial methods of parenteral administration. We particularly applied subcutaneous injection administration of those documented in the application. Other partial methods of parenteral administration of the composition according to this patent application e.g. intraperitoneal, intrathecal are further possible considered variants (Huynh, G. H., Deen, D. F., Szoka, F. C., J. Control. Rel., 110, 2006, 236-259). They are well manageable from formulation-technological point of view, however the exact immunological properties of all the substances used, i.e. immunologic purity of the components of the composition according to the invention and of course the appropriate biologic response will be decisive for their use.

The reasons for the above stressed non-invasive methods of administration of the composition according to the invention are except for others based on the facts that both sublingual and rectal mucous membranes represent substantially permeable and also well accessible biological barriers, through which even multimolecular medicines penetrate. The speeds of medicine effect commencement are completely satisfactory for the intended anti tumor effect. It is moreover well known that substances in this administration methods do not suffer from quick first-pass effect in the absorption biological membrane itself (unlike in the intestine wall) after absorption.

We consider the fact that we have found a combination of the anti-neoplastic composition and application vehicle that in rectal administration in in vivo experiments on nu/nu mice anti-tumor effect against a chosen tumor line, namely line A 549 of small-cell lung tumor showed significantly better results than in administration of the same doses of the same composition by subcutaneous injection, a real innovative finding. Transport of substances to the tumor affected place is probably more complicated after subcutaneous administration.

The solution proposed by us linked at present with sublingual administration method, which in principle enables as fast (or slightly faster) commencement of medicine effect as subcutaneous injection administration, is relatively advanced. Its basic advantage is that it ensures slower and longer transfer to the system circulation to substances with large molecule (e.g. 50,000). We can thus actually talk about sublingual infusion. Such sublingual administration has a substantial advantage against parenteral, including subcutaneous administration. This is the fact that substances after absorption through sublingual mucous membrane are not taken by the bloodstream directly to the liver, where they are mostly metabolised and deactivated, but they avoid the liver first-pass effect. The path and time of their movement in organism are thus much longer and enable non metabolised substances to reach to more distant parts of the body. This is why we consider sublingual method very advantageous also for administration of the anti-neoplastic composition according to the invention.

Quickly disintegrating and soluble sublingual tablets or quickly soluble lyophilised tablets, the technology of which is well described and practically applied, can be generally used for sublingual administration. This issue with further application forms like sprays, gels, pastes, plasters, films and strips is dealt with in details by the latest summary by V. Hearnden (Hearnden V. et al., Adv. Drug Deliv. Rev., 64, 2012, 16-28). In the case of biologics the swallowing reflex and inhibition of medicine by saliva content are the main problems of application of this method.

A brand new type of sublingual preparation (new dosage form) suitable for biologics due to its composition and properties is based on application of nanofiber membranes (Stranska, D. et al.: Pat CZ 303 244; 2012). By their design and by using suitable pharmaceutically acceptable polymers they help avoid usual problems of other sublingual products, particularly their interaction with saliva or swallowing substantial part of the medicine. These nanofiber membranes have excellent mechanical properties, they usually enable up to 50 percent of active substances, including biologics, to be incorporated directly into the fibers. Even higher weight percentage of active substances may be anchored by impregnation. In mass production they are advantageously produced e.g. by means of electrospinning. They usually use carrying and structural polymers from the group of polyvinyl alcohol, polylactide, polycaprolactone, polyvinylpyrrolidone, their copolymers, copolymer polyethylene glycol/polyvinyl caprolactam/polyvinyl acetate, cellulose derivates like e.g. hydroxypropyl cellulose, hydroxypropyl methylcellulose, dextranes of various molecular weights, isolated as well as in mixtures and also numerous polymerized monomers of mixtures of at least two of them. A variant where the active substances are integrated directly in the nanofiber material of the preparation active layer designed for the contact with mucous membrane, which is covered by another nanofiber layer, e.g. polyurethane (see Example 12) protecting the active substances against contact with saliva is the most important for the composition according to the invention.

Moreover, and this may be substantial, deposition of biologics in nanofibers is probably today's most prospective way of biologics stabilization. Compared to the demandingness of cryogenic techniques and spray technologies this method is considerate from the point of view of the minimum temperature and pressure load on the active substance and from the point of view of integration of its structure in the fiber carrier. (Klein, S. et al., Biomacromolecules 10, 2009, 1751-1756). Due to mass production technologies of electrostatic spinning the anti-neoplastic composition according to the invention may be factually processed not only into nanomembranes for direct application of the active substances, but also into stabilized intermediate product and biologics type products for stock, all that actually without loss of biological activity of the active substances (e.g. of protein, polypeptide, virus or bacteria type).

The rectal administration method provides the same advantages in terms of first-pass effect avoidance and longer transport range for nonmetabolised therapeutic molecules. Except for minor problems, which are absolutely negligible with regard to the sense and importance of rectal administration of the anti-neoplastic combination according to the invention, this method can be definitely considered advantageous as we have repeatedly demonstrated for the composition according to the invention by the above mentioned in vivo trials.

Rectal systemic administration of medicines is traditionally used, well proven, backed by relatively wide selection of excipients and suitable manufacturing technologies. It may use conventional excipients, i.e. non-ionic substances from the group containing neutral lipids, e.g. tri-, di- or monoesters of higher fatty acids and polyols, e.g. glycerol, polyoxyethylene glycerides, e.g. polyoxyethylene glycol glyceryl-cocoate, polyoxyethylene glycols, polyethylene glycol ethers and higher fatty alcohols, e.g. lauryl alcohol, polyoxyethylene polar oils, e.g. ricin oil, oil saccharoglycerides, polyethylene oxide and propylene oxide copolymers and their mixtures, if necessary with selected antioxidants (e.g. tocopherols, ascorbic acid, their derivatives like tocopheryl ascorbate) and further auxiliary substances.

"Co-administration" principle can be used to reach the effective levels of the anti-neoplastic composition in the organism. This means administration of all the composition parts in such amounts that ensure effect at the same time with regard to the application method or at different moments by means of one application preparation or more application preparations. This may be a single "co-administration" or multiple administrations at particular intervals. With the possibility to use various methods of administration a part of the composition may be administered by one of the possible methods (e.g. rectally) and the other part necessary to reach effective levels of the composition in the organism may be administered by different method, e.g. sublingually or parenterally.

Innovativeness

The essential innovation of the solution according to the invention is based on yet not described integration of lipase enzyme into an anti-neoplastic composition and its proven wide-spectral effectiveness. The newly designed composition of the preparation shows in in vivo trials a sum of activities bringing a complex, surprisingly strong cellular anti-tumoral effects. This finding is based on the results obtained from in vivo trials on nu/nu mice with subcutaneously implanted cells of standardized lines of human mammary carcinoma, colorectal carcinoma, pancreatic carcinoma and small-cell lung carcinoma.

Further innovation of the invention is in the composition definition based on enzymatic activity units, not on weight proportions of the individual active substances as it is in earlier remotely similar patents (Trnka et al, 1996, 1998, see above). This approach to efficiency definition ensures technical feasibility of the invention and reproducibility of composition of the active substances, and thus also of the appropriate manners designed for their administration to organism. Today's pharmacopoeias include requirement for using the activity characteristics for enzymes.

Further innovation of the solution according to the invention is in the fact that we have demonstrated and applied upon the achieved results advantageous non-invasive methods of administration and appropriate dosage systems for administration of the enzyme and proenzyme composition. Unlike in all the existing patents dealing with administration of biologics we have proposed preparations for non-invasive transmucosal administration in wide scale of indications of the anti-tumoral composition according to the invention. Surprisingly positive therapeutic results of rectal administration showed us the way to sublingual administration. This brings prospect of improved compliance for a patient and possibility of self-administration of the anti-neoplastic preparation.

Innovation of the solution is also in the fact that we define suitable vehicles for administration of the composition in direct relation to the chosen application way and also definite therapeutic, diagnostic or prophylactic requirements. Particularly polyethylene glycol of appropriate molecule weight or a mixture of selected polyethylene glycols (e.g. macrogol 300 and macrogol 1500 in weight ratio 45:55) or glycerol, N-propanol or trehalose and further saccharides (sucrose, mannitol) as structural stabilizers for proteins are advantageous excipients for the active substances individually as well as for their compositions. The solution according to the invention also considers application of polyethoxylated lipidic substances (e.g. stearoyl polyoxyl-6-glycerid), neutral lipids (e.g. glyceryl-palmitostearate), esters of monovalent alcohols with higher fatty acid (e.g. isopropyl-myristate, isopropyl-palmitate) in processing anhydrous pulverized anti-tumoral composition and permeation enhancers, e.g., glycerol, cyclopentadecanolide, polycarbophil-cysteine.

Innovation of the solution is also in preparation and use of the above structural and stabilizing excipients as well as the technology of electrostatic spinning for processing the individual components into a stabilized composition of proenzymes and enzymes as a formulating intermediate product (see Example 11, Example 12).

DESCRIPTION OF FIGURES

FIG. 1 presents a photo documentation of in vivo trial on nu/nu mice with MDA-MB-231 line of mammary carcinoma in 36-day rectal administration of composition K2 (dose 2, lipophilic vehicle) compared to the reference mouse (without administration).

FIG. 2 presents the average values of tumor volumes (including SD) during 40-day in vivo trial with MDA-MB-231 line in subcutaneous and rectal administration of the anti-neoplastic composition 2 (female nu/nu mice; approx. 28 g; 8 mice in each group; dose 2 contains double quantity of composition 2).

FIG. 3 presents a photo documentation of the first third of in vivo trial on nu/nu mice with H 116 line of colorectal carcinoma in everyday rectal administration of composition 2 (dose 1; lipophilic base) compared to the reference mouse (without administration).

FIG. 4 presents the average values of tumor volumes (including SD) up to the $23^{rd}$ day of in vivo trial on nu/nu mice with H 116 line of colorectal carcinoma in subcutaneous and rectal administration of the anti-neoplastic composition K1 (K2) (female nu/nu mice; approx. 28 g; 8 mice in each group).

FIG. 5 presents a photo documentation of in vivo trial with CAPAN 2 line of pancreatic carcinoma on nu/nu mice in 85-day of subcutaneous rectal administration of the composition K2 compared to the reference mouse (without administration).

FIG. 6 presents the average values of tumor volumes (including SD) v in vivo trial on nu/nu mice with CAPAN 2 line of pancreatic carcinoma in everyday subcutaneous and rectal administration of anti-neoplastic composition K1, or K2; (female nu/nu mice; approx. 28 g; 8 mice in each group).

FIG. 7 presents a photo documentation of 75-day (99-day) in vivo trial with A 549 line of small-cell lung carcinoma on nu/nu mice in everyday rectal administration of composition 2 (hydrophilic base, dose 2) compared to the reference mouse (without administration).

FIG. 8 presents the average values of tumor volumes (including SD) in 75-day (99-day) in vivo trial on nu/nu mice with A 549 line of small-cell lung carcinoma in everyday subcutaneous and rectal administration of anti-neoplastic composition K1, resp. K2 (female nu/nu mice; approx. 28 g; 8 mice in each group; dose 2 is double quantity of dose 1).

EXAMPLES OF EMBODIMENT

Figure 1:
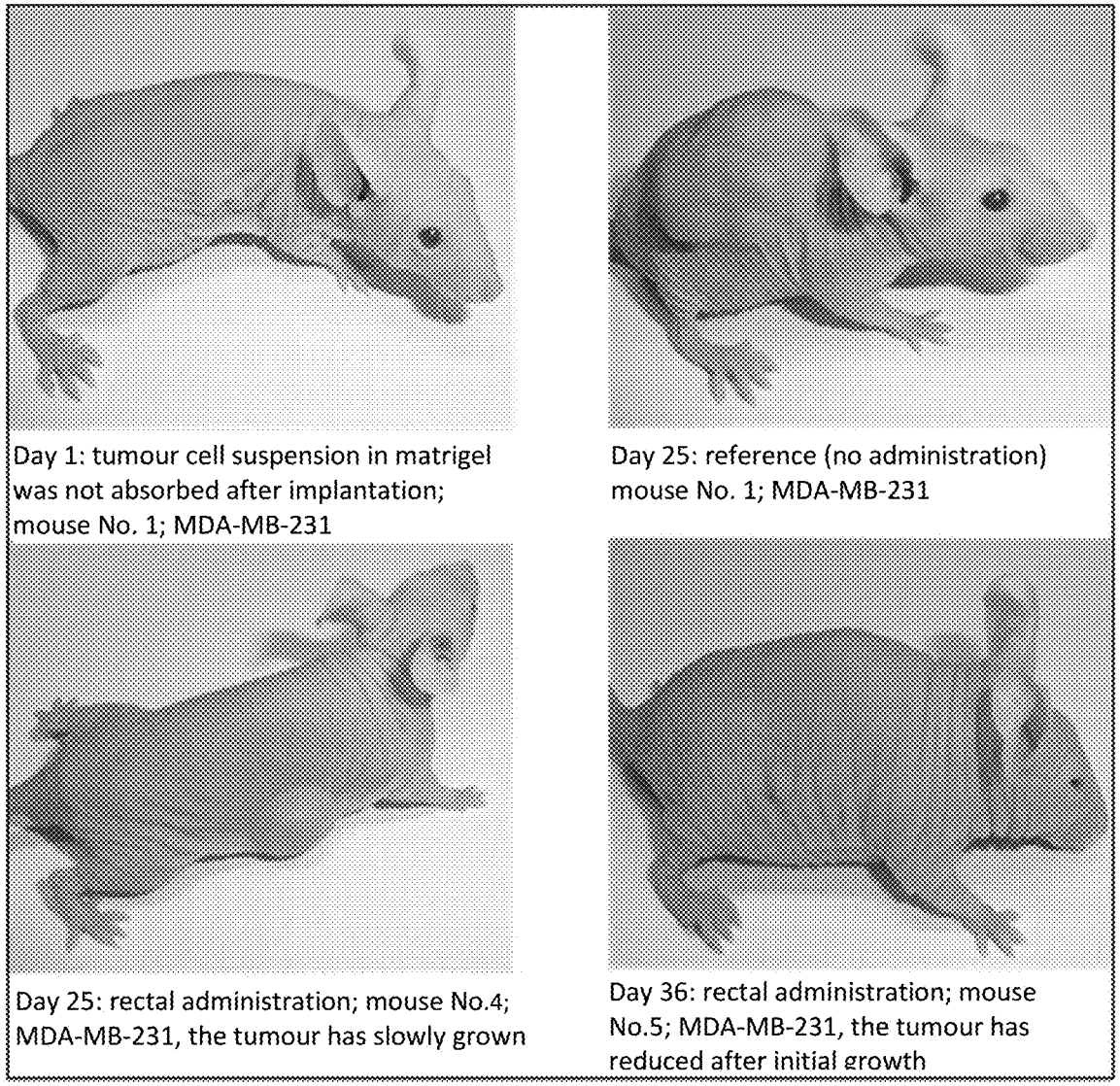
FIG. 1 shows a part of photo documentation visually comparing the treated and untreated mouse with subcutaneously transplanted MDA-MB-231 line of mammary carcinoma in 36-day in vivo trial in everyday rectal administration of the anti-neoplastic composition. Particularly.
Figure 2:
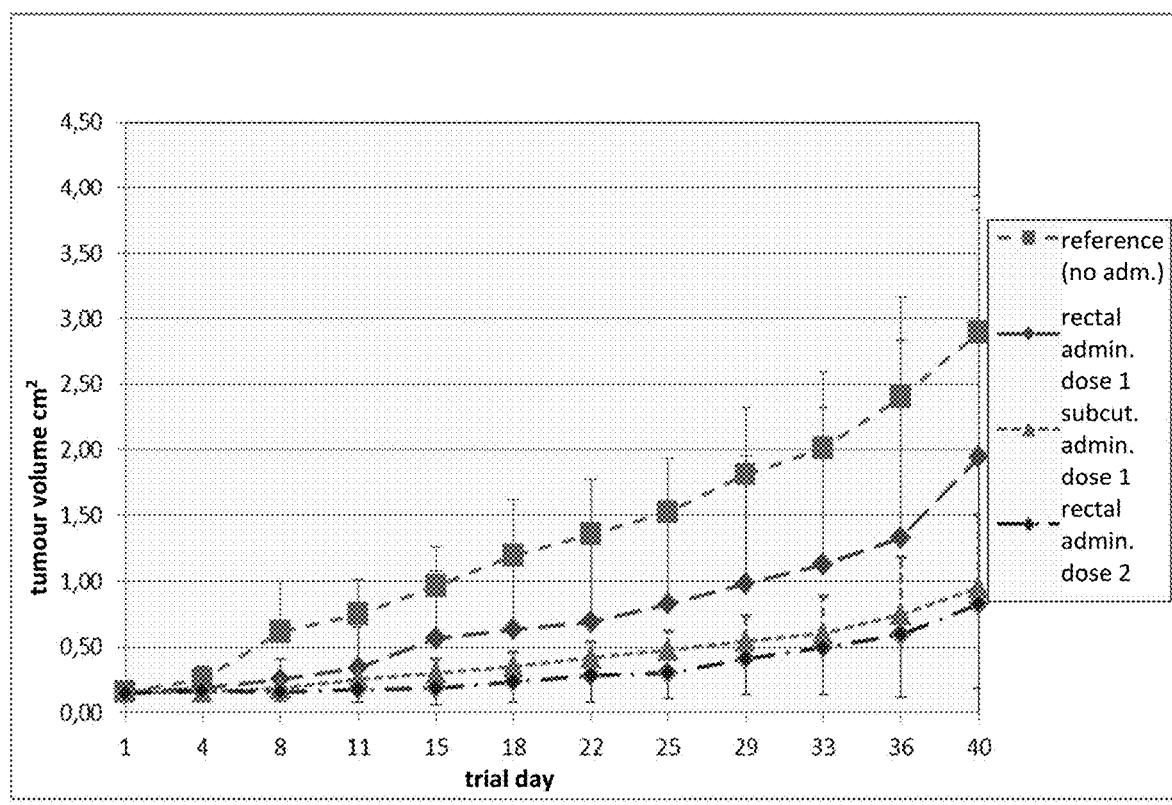
FIG. 2 shows graphic interpretation of average values of tumor volumes (including SD) in 36-day in vivo trial on nu/nu mice with subcutaneously transplanted MDA-MB-231 line of mammary carcinoma in everyday subcutaneous and rectal administration of the anti-neoplastic composition according to this application (composition K1, or K2 according to Table 1); female nu/nu mice; approx. 28 g; 8 mice in each group; lipophilic suppository vehicle; dose 2 represents double quantity of K2 composition. Particularly.
Figure 3:
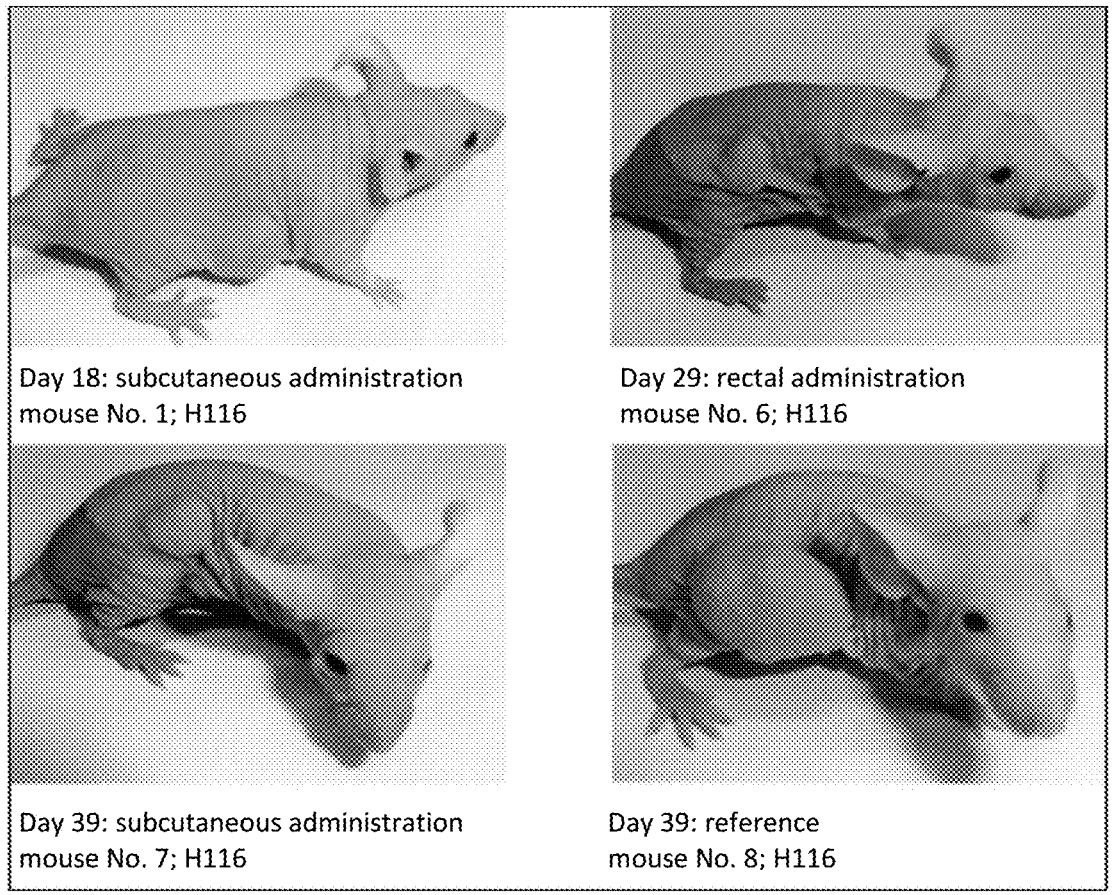
FIG. 3 shows a part of photo documentation visually comparing the treated and untreated mouse with subcutaneously transplanted H 116 line of colorectal carcinoma in 75-day in vivo trial in everyday rectal and subcutaneous administration of the anti-neoplastic composition. Particularly.
Figure 4:
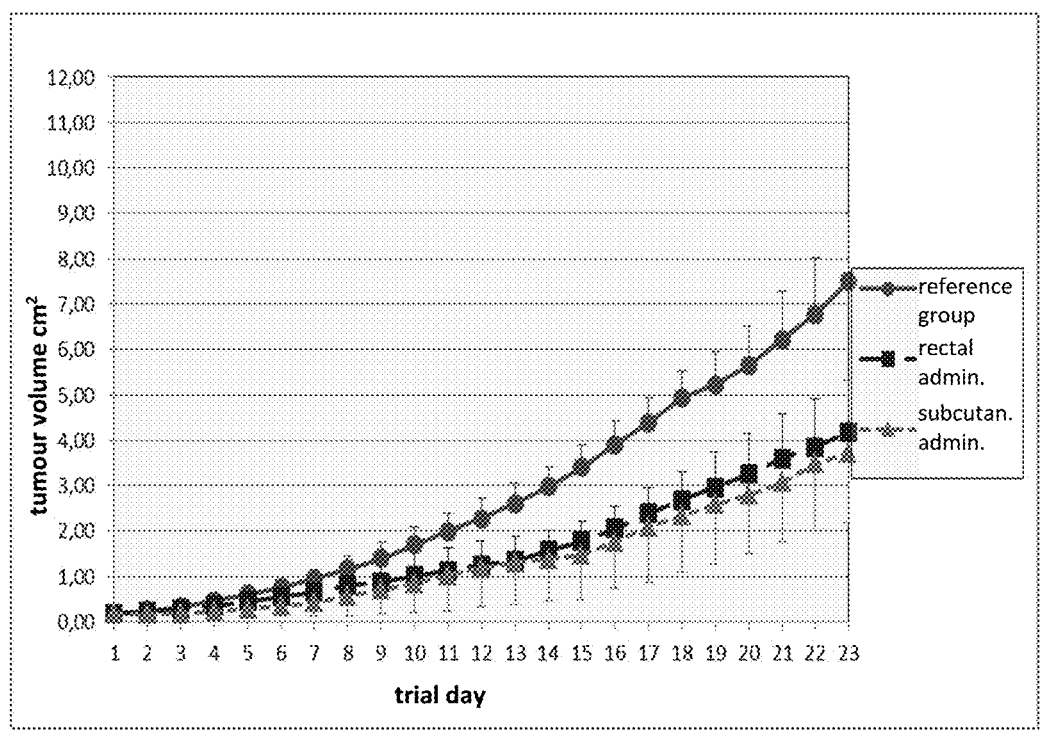
FIG. 4 shows graphic interpretation of average values of tumor volumes (including SD) in 75-day in vivo trial on nu/nu mice with subcutaneously transplanted H 116 line of colorectal carcinoma in everyday subcutaneous and rectal administration of the anti-neoplastic composition according to this application; female nu/nu mice; approx. 28 g; 8 mice in each group; lipophilic suppository vehicle. Particularly.
Figure 5:
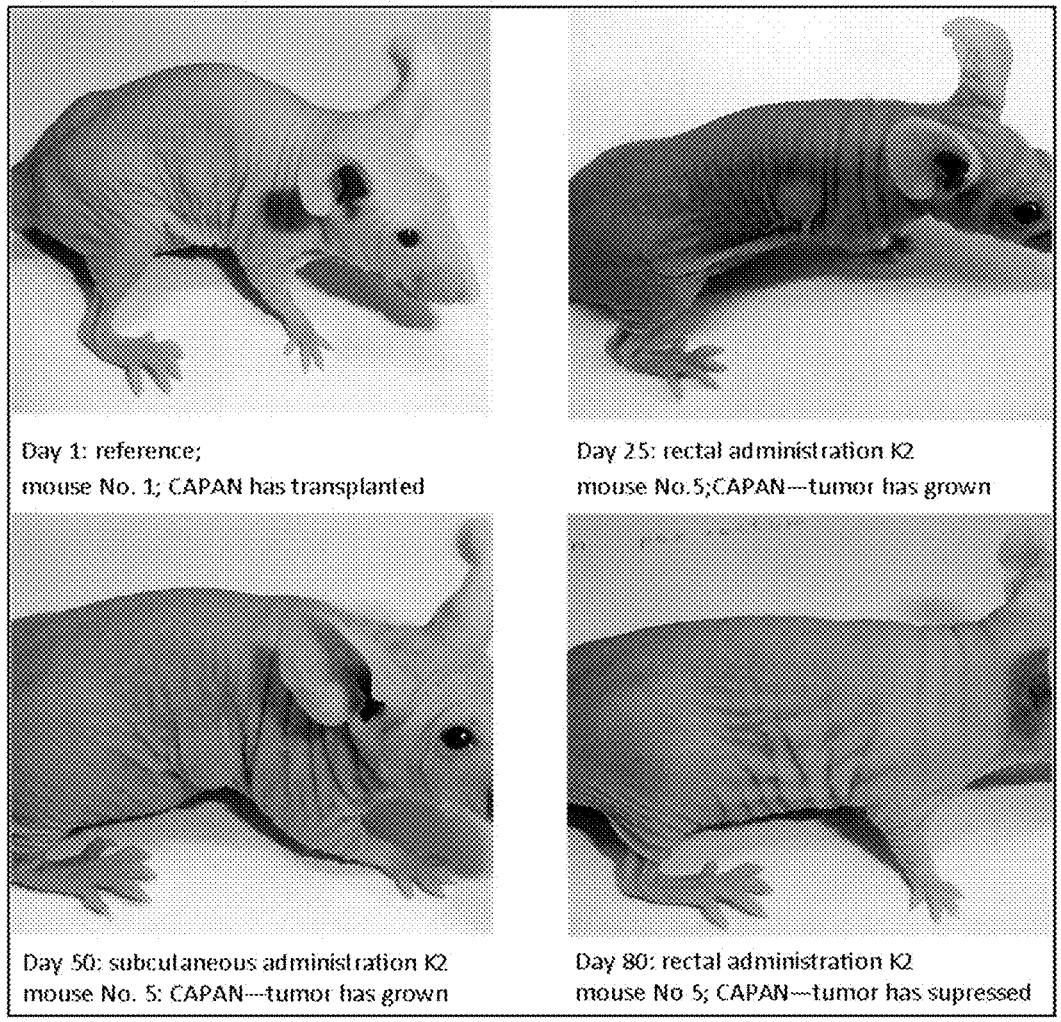
FIG. 5 shows a part of photo documentation visually comparing the treated and untreated mouse with subcutaneously transplanted CAPAN 2 line of pancreatic carcinoma in 85-day in vivo trial in everyday subcutaneous and rectal administration of the anti-neoplastic composition. Particularly.
Figure 6:
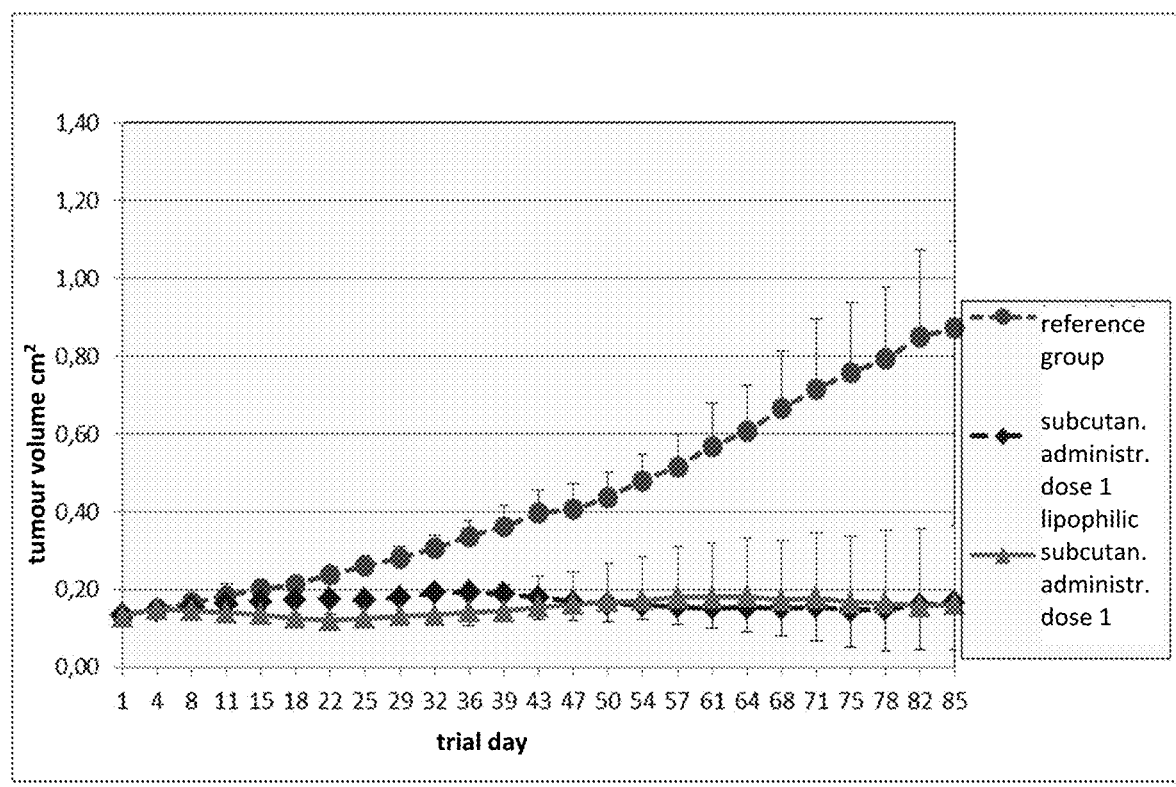
FIG. 6 shows graphic interpretation of average values of tumor volumes (including SD) in 85-day in vivo trial on nu/nu mice with subcutaneously transplanted CAPAN 2 line of pancreatic carcinoma in everyday subcutaneous and rectal administration of the anti-neoplastic composition according to this application; female nu/nu mice; approx. 28 g; 8 mice in each group; lipophilic suppository vehicle. Particularly.
Figure 7:
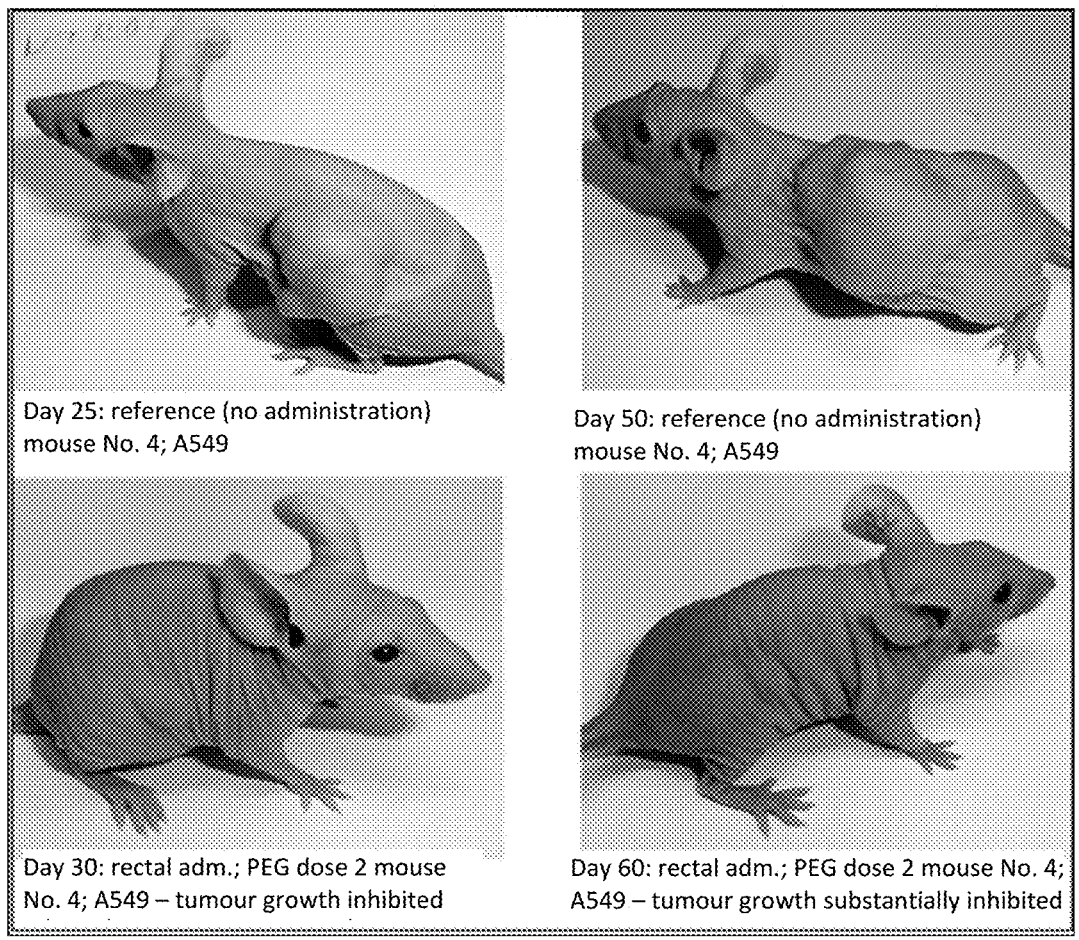
FIG. 7 shows a part of photo documentation visually comparing treated and untreated mouse with subcutaneously transplanted A 549 line of small-cell lung carcinoma on the 50th and 60th day of in vivo trial in everyday administration of the anti-neoplastic composition. Particularly.
Figure 8:
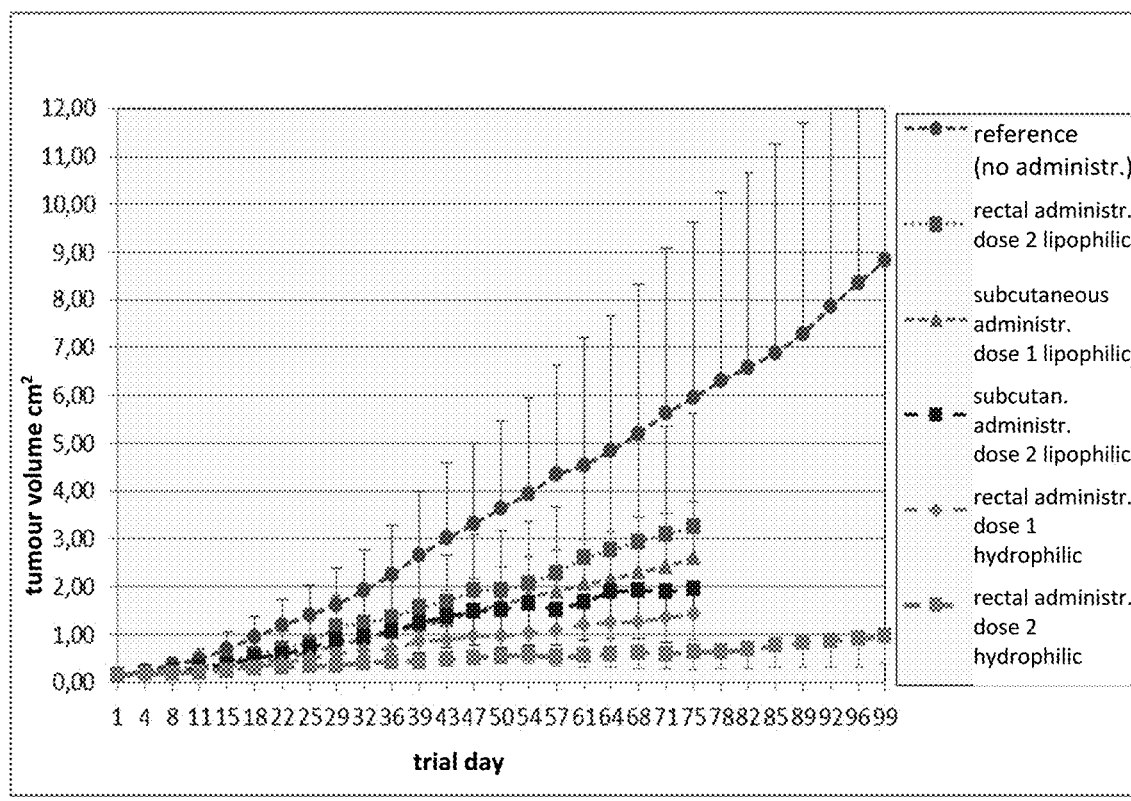
FIG. 8 shows graphic interpretation of average values of tumor volumes (including SD) in an in vivo trial with subcutaneously transplanted A 549 line of small cell lung carcinoma in everyday rectal administration of the anti-neoplastic composition (K2 according to Table 1) female nu/nu mice; approx. 28 g; 8 mice in each group; hydrophilic suppository vehicle. Particularly.

Example 1: Qualitative Structure of the Anti-Neoplastic Composition According to the Invention Application 1. Amylase: Alpha-amylase from *Bacillus* sp. Type II-A, lyophilised powder. Isolated from *Bacillus amyloliquefaciens*. Sigma-Aldrich. Prague. Product No.: A 6380; EC No. (Sigma): 232-560-9; EC No.: 3.2.1.1; CAS No.: 9000-90-2

Molecular weight: 58,403

Activity: 1,333 i.u./mg of solid substance; 3,100 m.j/mg of protein

2. Lipase: Lipase from wheat germ, Type I; lyophilised powder. Isolated from *Triticium aestivum*. Sigma-Aldrich. Prague. Product No.: L 6380, EC No. (Sigma): 232-619-9 EC 3.1.1.3; CAS No.: 9001-62-1

Molecular weight: 143,000

Activity: 5-15 i.u./mg of protein

3. Chymotrypsinogen: α-Chymotrypsinogen A from bovine pancreas. lyophilised powder, without salt content. Applichem. Prague. Product No.: A069

CAS No.: 9035-75-0

Molecular weight: approx. 25,000

Activity: min. 1,200 i.u./mg

4. Trypsinogen: Trypsinogen from bovine pancreas. Dialyzed and lyophilised powder, without salt content. Sigma-Aldrich. Prague. Product No.: T1143; EC No. (Sigma): 232-651-3;

CAS No.: 9002-08-8

Molecular weight: 23,700

Activity: 10,900 i.u./mg of protein

TABLE 1

Examples of proportional weight combination of parts of the anti-neoplastic composition for formulation of the preparations for various administration methods. Qualitative composition is in Example 1.

| | Identification | | | | |
|---|---|---|---|---|---|
| | Composition 1 | Composition 2 | Composition 3 | Composition 4 | Composition 5 |
| | Method of Administration | | | | |
| | Subcutaneous | Rectal | Sublingual | Inhalation | Intraperitoneal |
| | Quantity | | | | |
| | mg | mg | mg | mg | mg |
| Amylase | 2.07 | 4.07 | 5.6 | 1.95 | 9.6 |
| Lipase | 2.89 | 9.89 | 12.8 | 9.89 | 12.2 |
| Chymotrypsinogen | 10.24 | 14.24 | 14.24 | 28.5 | 14.2 |
| Trypsinogen | 29.58 | 22.32 | 29.58 | 14.24 | 35.0 |

The individual components of the composition can be processed according to usual rules as powder mixture and then as an intermediate product towards the required dosage form. Individual finely ground components may also be gradually integrated to a prepared vehicle or its part for the purpose of primary processing with suitable carrier (e.g. trehalose for injection administration, see Example 12, stabilizing excipient (e.g. n-propanol, polyethylene glycol 300) or complete vehicle (hardened fat with added isopropylmyristate as suppository base) according to particular intended application (see Example 8 and Example 9)

In processing and in possible storage of the compositions requirements of the manufacturers of the individual components have to be kept. (e.g. temperature, humidity, protective atmosphere, ambient purity).

Specific quantity of the therapeutic composition required for administration of one dose to a human depends on characteristics of the particular individual (weight, age, health condition parameters including individual reactivity to the administered composition), anti-neoplastic disease characteristics (e.g. type, location, stage) administration method (e.g. systemic sublingual, parenteral infusion, systemic rectal), way of application (e.g. monotherapeutic, sequential, graded) and preparation physical character (e.g. colloid solution, separated powder mixture).

Examples 2.1, 3.1, 4.1, and 5.1 represent sequences of amino acids of enzymatic and proenzymatic substances for anti-neoplastic compositions according to Example 1 and Table 1. Related reference examples 2.2, 2.3, 3.2 to 3.4, 4.2, and 5.2 represent sequences of amino acids of representatives of biologically similar substances that may be used as substitutes for substances according to Table 1 as so called "biosimilars" namely individually or in the complete structure. Maintaining the effect quality the individual enzymatic activities of the components in relation to protein weight unit are always important for such biologically similar compositions prepared this way. This characteristic is one of the factors deciding on suitability of an alternative "biosimilar" composition for a particular or considered application.

The examples in principle illustrate the possibility of substitution of partial substances, both, by biologically similar isolated natural substances or biotechnologically produced substances.

Example 2.1: SEQ ID NO: 1 (Sequence of Amino Acids of Alpha-Amylase, *Bacillus* Species, *Amyloliquefaciens*)(Further See Table 1)

```
  1  MIQKRKRTVS FRLVLMCTLL FVSLPITKTS AVNGTLMQYF EWYTPNDGQH WKRLQNDAEH
 61  LSDIGITAVW IPPAYKGLSQ SDNGYGPYDL YDLGEFQQKG TVRTKYGTKS ELQDAIGSLH
121  SRNVQVYGDV VLNHKAGADA TEDVTAVEVN PANRNQETSE EYQIKAWTDF RFPGRGNTYS
181  DFKWHWYHFD GADWDESRKI SRIFKFRGEG KAWDWEVSSE NGNYDYLMYA DVDYDHPDVV
241  AETKKWGIWY ANELSLDGFR IDAAKHIKFS FLRDWVQAVR QATGKEMFTV AEYWQNNAGK
301  LENYLNKTSF NQSVEDVPLH FNLQAASSQG GGYDMRRLLD GTVVSRHPEK AVTFVENHDT
361  QPGQSLESTV QTWFKPLAYA FILTRESGYP QVFYGDMYGT KGTSPKEIPS LKDNIEPILK
421  ARKEYAYGPQ HDYIDHPDVI GWTREGDSSA AKSGLAALIT DGPGGSKRMY AGLKNAGETW
481  YDITGNRSDT VKIGSDGWGE FHVNDGSVSI YVQ
```

Reference Example 2.2: SEQ ID NO: 2 (Sequence of Amino Acids of Biologically Similar (90%) α-Amylase, *Triticum urartu* (Red Wild Einkorn), (*Crithodium Urartu*))

```
  1  MERRGLLKAA LLASCLLVVC SGRVPTVIQQ PSTTIYNSTL AKTLVEYAAA IYTADLTQLF
 61  TWTCDRCGDL IEGFEMMDII VDVESCLEAY VGFASDINAV VVVFRGTQEN SIQNWIEDLL
101  WKQLDLDYPG MPEAMVHRGF YSAYHNTTIR DGIVSGIQKT QKLHGDVPIM VTGHSMGAAM
151  ASFCALDLVV NYGLDDVKLM TFGQPRVGNA AFASYLKRYL PHAIRVTNAND IVPHLPPYF
201  SFFPQKTYHH FPREVWVHDV GLGSLVYTVE QICDDSGEDP ACSRSVSGNS IQDHITYLGV
301  SMHAEAWSSC RIVMDYAELR YKMDLHGNVV LSKQQQQSGL SNERRRHSAQ
```

Reference Example 2.3: SEQ ID NO: 3 (Sequence of Amino Acids of Biologically Similar (90%) α-Amylase, *Bacillus lichenformis*)

```
  1  MKQQKRLYAR LLTLLFALIF LLPHSAAAAA NLNGTLMQYF EWYMPNDGQH WKRLQNDSAY
 61  LAEHGITAVW IPPAYKGTSQ ADVGYGAYDL YDLGEFHQKG TVRTKYGTKG ELQSAIKSLH
121  SRDINVYGDV VINHKGGADA TEDVTAVEVD PADRNRVISG EHRIKAWTHF HFPGRGSTYS
181  DFKWHWYHFD GTDWDESRKL NRIYKFQGKA WDWEVSNENG NYDYLMYADI DYDHPDVAAE
241  IKRWGTWYAN ELQLDGFRLD AVKHIKFSFL RDWVNHVREK TGKEMFTVAE YWQNDLGALE
301  NYLNKTNFNH SVFDVPLHYQ FHAASTQGGG YDMRKLLNST VVSKHPLKAV TFVDNHDTQP
361  GQSLESTVQT WFKPLAYAFI LTRESGYPQV FYGDMYGTKG DSQREIPALK HKIEPILKAR
421  KQYAYGAQHD YFDHHDIVGW TREGDSSVAN SGLAALITDG PGGAKRMYVG RQNAGETWHD
480  ITGNRSEPVV INSEGWGEFH VNGGSVSIYV QR
```

Example 3.1: SEQ ID NO: 4 (Sequence of Amino Acids of Lipase, *Tritici aestivum* (See Table 1))

```
  1  MERRGLLKTA LLACLLVVCS GRVPMVIQQP STTIYNSTLA KTLVEYAAAI YTADLTQLFT
 61  WTCDRCGDLI EGFEMMDIIV DVENCLEAYV GFASDINAVI VVFRGTQENS IQNWIEDLLW
121  KQLDLDYPGM PEAMVHRGFY SAYHNTTIRD GIVSGIQKTR KLHGDVPIMV TGHSMGAAMA
181  SFCALDLVVN YGLDDVKLMT FGQPRVGNAA FASYFKRYLP HAIRVTNAND IVPHLPPYFS
241  FFPQKAYHHF PREVWVHDVG LGSLVYTVEQ ICDDSGEDPA CSRSVSGNSI QDHITYLGVS
301  MHAEAWSSCR IVMDYAELRY KMDLHGNVVL SKQQQQQPGL SDQRRRHSAQ
```

Reference Example 3.2: SEQ ID NO: 5 (Sequence of Amino Acids of Biologically Similar Lipase, *Sus Scrofa*)

```
  1  SEVCFPRLGC FSDDAPWAGI VQRPLKILPW SPKDVDTRFL LYTNQNQNNY QELVADPSTI
 61  TNSNFRMDRK TRFIIHGFID KGEEDWLSNI CKNLFKVESV NCICVDWKGG SRTGYTQASQ
121  NIRIVGAEVA YFVEVLKSSL GYSPSNVHVI GHSLGSHAAG EAGRRTNGTI ERITGLDPAE
181  PCFQGTPELV RLDPSDAKFV DVIHTDAAPI IPNLGFGMSQ TVGHLDFFPN GGKQMPGCQK
241  NILSQIVDID GIWEGTRDFV ACNHLRSYKY YADSILNPDG FAGFPCDSYN VFTANKCFPC
301  PSEGCPQMGH YADRFPGKTN GVSQVFYLNT GDASNFARWR YKVSVTLSGK KVTGHILVSL
361  FGNEGNSRQY EIYKGTLQPD NTHSDEFDSD VEVGDLQKVK FIWYNNNVIN PTLPRVGASK
421  ITVERNDGKV YDFCSQETVR EEVLLTLNPC
```

Reference Example 3.3: SEQ ID NO: 6 (Sequence of Amino Acids of Biologically Similar Lipase (50%), *Oryza sativa Japonica* Group)

```
  1  MSSSPMLGGI ADRWRELHGQ DSWNGLLDPL DLDLRSSILS YGELVQATYD SFNRERRSPH
 61  AGACVYGHGD LLAAAGASAA GSYAVTKFVY ATSGLPVPEA FLLLPLPSLL PPAWSRESNW
121  MGYVAVATDE GVAALGRRDI VVAWRGTVES LEWVNDFDFT PVPAAPVLGA AAAANPRAIV
181  HRGFLSVYTS SNKDSKYNKA SARDQVLEEV RRLMELYKDE VTSITVVGHS LGASLATLNA
241  VDIVANGANC PPASSSSSQP PCPVTAIVFA SPRVGDGFFK AAFASFPDLR ALHVKNAGDV
301  VPMYPPLGYV DVAVKLRIST SRSPYLRSPG TIETLHNLEC YLHGVAGEQG SAGGFKLEVD
361  RDVALANKGV DALKDKYPVP PRWWVSKNRC MVKDADGHWA LHDFEQI
```

Reference Example 3.4: SEQ ID NO: 7 (Sequence of Amino Acids of Biologically Similar Lipase, *Bifidobacterium animalis* Subsp. *Lactis* DSM 10140)

```
  1  MELYRNNEIP PIEYTPGTSE FRDAVIGLAR YWTAIAEDLH ADEPGVQERT AAACLRFRKE
 61  CAMFDYARAL QWHDPQGVYV HTDIPYLPDG GYRDGEVRGH LLDVYIPRDA IVRGGNTLPV
121  YIDIHGGGFT YGYKELNRNF NTHLADLGFG VFSLNYRPAP QTDLVGQLHD IQAALCWIGE
181  HITQFPVSPD NIFITGDSAG ACLSLLTLLI EHNDDAAHAF GIERASGIHL RGASLISGVY
241  DITPSSPMRA RLAETVGNEF FAGLDDATVF LDPADWLTQG IGIPPLFLVT SSDDFVQSET
301  LALATSLARN GRDFELHDFK VPCTQTLGHV FPVGMTWLPE SERVLHGIRE FSYPLTR
```

Example 4.1: SEQ ID NO: 8 (Sequence of Amino Acids of Trypsinogen, *Bos Taurus* (See Table 1) Chain A:)

```
  1  VDDDDKIVGG YTCGANTVPY QVSLNSGYHF CGGSLINSQW VVSAAHCYKS GIQVRLGEDN

61  INVVEGNEQF ISASKSIVHP SYNSNTLNND IMLIKLKSAA SLNSRVASIS LPTSCASAGT

121  QCLISGWGNT KSSGTSYPDV LKCLKAPILS DSSCKSAYPG QITSNMFCAG YLEGGKDSCQ

181  GDSGGPVVCS GKLQGIVSWG SGCAQKNKPG VYTKVCNYVS WIKQTIASN
```

Reference example 4.2: SEQ ID NO: 9 (Sequence of amino acids of biologically similar trypsinogen I Sequence 2, Patent U.S. Pat. No. 7,049,484, 2006)

```
  1  VDDDDKIVGG YTCGANTVPY QVSLNSGYHF CGGSLINSQW VVSAAHCYKS GIQVRLGEDN

61  INVVEGNEQF ISASKSIVHP SYNSNTLNND IMLIKLKSAA SLNSRVASIS LPTSCASAGT

121  QCLISGWGNT KSSGTSYPDV LKCLKAPILS DSSCKSAYPG QITSNMFCAG YLEGGKDSCQ

181  GDSGGPVVCS GKLQGIVSWG SGCAQKNKPG VYTKVCNYVS WIKQTIASN
```

Examples 5.1: Sequence of amino acids of chymotrypsinogen A, *Bos taurus* (see Table 1) SEQ ID NO: 10 (Chain A)

```
  1  CGVPAIQPVL SGLSRIVNGE EAVPGSWPWQ VSLQDKTGFH FCGGSLINEN WVVTAAHCGV

61  TTSDVVVAGE FDQGSSSEKI QKLKIAKVFK NSKYNSLTIN NDITLLKLST AASFSQTVSA

121  VCLPSASDDF AAGTTCVTTG WGLTRYTNAN TPDRLQQASL PLLSNTNCKK YWGTKIKDAM

181  ICAGASGVSS CMGDSGGPLV CKKNGAWTLV GIVSWGSSTC STSTPGVYAR VTALVNWVQQ

241  TLAAN
```

SEQ ID NO: 11 (Chain B)

```
  1  CGVPAIQPVL SGLSRIVNGE EAVPGSWPWQ VSLQDKTGFH FCGGSLINEN WVVTAAHCGV,

61  TTSDVVVAGE FDQGSSSEKI QKLKIAKVFK NSKYNSLTIN NDITLLKLST AASFSQTVSA

121  VCLPSASDDF AAGTTCVTTG WGLTRYTNAN TPDRLQQASL PLLSNTNCKK YWGTKIKDAM

181  ICAGASGVSS CMGDSGGPLV CKKNGAWTLV GIVSWGSSTC STSTPGVYAR VTALVNWVQQ

241  TLAAN
```

Reference Example 5.2: SEQ ID NO: 12 (Sequence of Amino Acids of Biologically Similar Chymotrypsinogen B (Synthetic Construct, CDS Clone))

```
  1  MAFLWLLSCW ALLGTTFGCG VPAIHPVLSG LSRIVNGEDA VPGSWPWQVS LQDKTGFHFC

61  GGSLISEDWV VTAAHCGVRT SDVVAGEFD QGSDEENIQV LKIAKVFKNP KFSILTVNND

121  ITLLKLATPA RFSQTVSAVC LPSADDDFPA GTLCATTGWG KTKYNANKTP DKLQQAALPL

181  LSNAECKKSW GRRITDVMIC AGASGVSSCM GDSGGPLVCQ KDGAWTLVGI VSWGSDTCST

241  SSPGVYARVT KLIPWVQKIL AAN
```

Reference Example 5.3: SEQ ID NO: 13 (Sequence of Amino Acids of Biologically Similar Chymotrypsinogen B, *Gadus morhua*)

```
  1  MGHEVDSVLP GLFRRTYGCG RPAISPVITG YSRIVNGEEA VPHSWSWQVS LQDQTGFHFC

61  GGSLINENWV VTAAHCNVKN YHRVVLGEHD RSSNSEGVQV MTVGQVFKHP RYNGFTINND

121  ILLVKLATPA TLNMRVSPVC LAETDDVFEG GMKCVTSGWG LTRYNAADTP ALLQQAALPL

181  LTNEQCKKFW GNKISDLMIC AGAAGASSCM GDSGGPLVCQ KAGSWTLVGI VSWGSGTCTP

241  TMPGVYARVT ELRAWVDQTI AAN
```

Example 6: Preparation with Anti-Neoplastic Composition 1 for Injection Intravenous Administration for Human Mammary Carcinoma Treatment Formula (g) for 100 doses

| | |
|---|---|
| Composition 1 | 2.239 |
| Trehalose | 25.00 |

The mixture is prepared as mixture lyophilised powder containing Composition 1 as per Table 1 with structural stabilizing trehalose, subsequently aseptically distributed in 100 vials. Preparation packing contains an ampoule with water vehicle of this content (mg/100 ml):

| | |
|---|---|
| Hydrogen sodium phosphate, dihydrate | 167 mg |
| Potassium dihydrogen phosphate | 20 mg |
| Potassium chloride | 20 mg |
| Sodium chloride | 800 mg |
| Polysorbate 80 | 10 mg |
| Polyethylene glycol 300 | 3.0 ml |
| Water for injection | to 100.0 ml |

Water vehicle is for ex tempore preparation of 3 millilitres of solution from dry lyophilised powder. Appropriate dose of Composition 1 in the resulting solution of volume 3 millilitres is then applied by droplet infusion of suitable composition e.g. with dextran 10,000.

Specific therapeutic, diagnostic or prophylactic dosage of the composition is based on complex oncologic examination of particular individual.

Example 7: Preparation with Anti-Neoplastic Composition for Injection Subcutaneous Administration for Human Mammary Carcinoma Treatment Formula (g) for 100 doses

| | | |
|---|---|---|
| Composition 1 | 2.580 | (see Tab. 1) |
| Polyethylene glycol 4000 | 5.160 | |

The mixture is prepared as mixture lyophilised powder containing Composition 1 as per Table 1 and stabilizing polyethylene glycol 4000 and subsequently aseptically distributed in 100 vials. Preparation packing contains an ampoule with solution of 8 mg of sodium chloride in 1 ml of water for injection.

Specific therapeutic, diagnostic or prophylactic dosage of the composition is based on complex oncologic examination of particular individual.

Example 8: Preparation with Anti-Neoplastic Composition for Human Colorectal Carcinoma Treatment for Rectal Administration by Lipophilic Suppository Formula (g) for 100 suppositories

| | |
|---|---|
| Composition 2 | 2.563 |
| Isopropyl-palmitate or Stearoyl polyoxyl-6-glyceride | 1.9 |
| Hardened fat | 180.0 |

Procedure:
1. Stirring slowly in a suitable vessel melt mixture of hydrogenated glycerides from coco oil to about 35° C. producing homogenous dispersed phase.
2. Mix gradually the same weight quantity of tempered isopropyl-myristate or stearoyl-polyoxyl-6-glyceride to well homogenized mixture of Composition 2 according to Table 1 in another vessel once producing a concentrated premix.
3. Stirring slowly add gradually the melted lipophilic dispersed phase to the homogenized premix.
4. Continue stirring at temperature below 35° C. for at least 15 minutes, then still slowly stir and let it cool to temperature between 30° C. and 31° C.
5. Then pour the suppository mass with the content of anti-neoplastic composition to prepared suppository mold forming suppositories of about 1.8 grams each.
6. Continue stirring the suppository substance when pouring into the forms to prevent the composition from sedimentation but not aerating the melt.

Protective atmosphere may be used if necessary.

The above Composition 2 is administered as a hydrophobic suppository in one morning dose.

Specific therapeutic, diagnostic or prophylactic dosage of the composition is based on complex oncologic examination of particular individual.

Example 9: Preparation with Anti-Neoplastic Composition for Human Small-Cell Lung Carcinoma Treatment for Rectal Administration by Hydrophilic Suppository Formula (g) for 100 suppositories

| | |
|---|---|
| Composition 2 | 2.563 |
| n-propanol or glycerol | 1.9 |
| Polyethylene glycol 300 | 95.0 |
| Polyethylene glycol 1500 | 85.0 |

1. Stirring slowly in a suitable vessel melt mixture of polyethylene glycol 300 and polyethylene glycol 1500 to 40° C. producing homogenous dispersed phase.
2. Mix gradually the same weight quantity of n-propanol or glycerol to well homogenized mixture of Composition 2 according to Table 1 in another vessel producing concentrated suspension.
3. Stirring slowly add gradually the melted hydrophilic dispersed phase to the homogenized suspension.
4. Continue stirring at temperature below 35° C. for at least 15 minutes, then let it cool to temperature between 30° C. and 31° C. under slow stirring.
5. Then pour the suppository substance with the anti-neoplastic Composition 2 to prepared suppository mold of forming suppositories about 1.8 grams each.
6. Continue stirring the suppository substance when pouring into the forms to prevent the composition from sedimentation but not aerating the melt.

The above Composition 2 according to Table 1 is administered as a hydrophilic suppository in one morning dose, or in a half dose in the morning and half dose at noon.

Specific therapeutic, diagnostic or prophylactic dosage of the composition is based on complex oncologic examination of particular individual.

Example 10: Preparation with Anti-Neoplastic Composition 3 for Human Pancreatic Carcinoma Treatment for Sublingual Administration Formula of nanofibrous membrane (g) for 100 applications

| | |
|---|---|
| Composition 3 | 3.11 |
| Trehalosa | 10.0 |
| Glycerol 85% buffered to pH 7.4 | 3.5 |
| Hydroxypropyl methyl cellulose | 2.2 |
| Polyethylene glycol 400 | 1.1 |
| Redistilled water | q.s. |

Procedure:
1. Prepare concentrated mixture of Composition 3 according to Table 1 with glycerol buffered to pH 7.4 in a suitable vessel.
2. Prepare solution of trehalose, polyethylene glycol 400 and hydroxypropyl methyl cellulose in water vehicle in another vessel.
3. Add gradually the trehalose solution as per 2 to the spread of Composition 3, stir thoroughly and put it in the supply bin of the manufacturing device NS WS 50 (Elmarco, Liberec, CZ).
4. Ionic composition of the bin content is optimized for electrospinning process.
5. After the check of conductivity and process parameters spin the prepared solution at temperature not exceeding 45° C. producing nanofibrous membrane that is anchored on the base material belt.
6. In the next cycle relay the nanofibrous membrane in analogical process from the solution of hydroxymethyl propyl cellulose and polyethylene glycol 400.
7. Form the combined two-layer nanomembrane according to the produced square weight of Composition 3 in nanofibrous membrane and according to the required dose, namely to strips of 10 cm² each.
8. The strip determined for single administration is adjusted in a storing part of suitable packaging.

The nanofibrous sublingual preparation is administered in the morning and in the evening after meal as adhesive film on the bottom side of tongue.

Specific dosage of the composition is based on complex oncologic examination of particular individual.

Example 11: Preparation with Anti-Neoplastic Composition 3 for Human Pancreatic Carcinoma Treatment for Sublingual Administration Formula of nanofibrous membrane (g) for 100 applications

| | |
|---|---|
| Composition 3 | 3.11 |
| Mannitol | 10.0 |
| n-propanol buffered to pH 7.4 | 3.5 |
| Polyvinyl alcohol | 2.2 |
| Polyethylene oxide 400 | 1.1 |
| Polyurethane | 0.9 |
| Redistilled water | q.s. |

Procedure: Analogous to Example 9. Relaying of the nanofibrous reservoir is performed by electrospinning of water insoluble polyurethane.

The resulting two-layer preparation is applied by the protective polyurethane layer towards the mouth cavity and by the hydroxypropyl methyl cellulose reservoir of Composition 3 to the sublingual side.

The nanofibrous sublingual preparation is administered in the morning and in the evening after meal as adhesive film on the bottom side of tongue.

Specific therapeutic, diagnostic or prophylactic dosage of the composition is based on complex oncologic examination of particular individual.

Example 12: Preparation with Anti-Neoplastic Composition 4 for Human Small-Cell Lung Carcinoma Treatment for Inhalation Administration Formula (g) of powder for 100 inhalations

| | |
|---|---|
| Composition 4 | 2.73 |
| Trehalose | 20.00 |
| Water for injection | to 100.0 |

Procedure:
1. Solve the weight quantity of Composition 4 in 100 g 20% (weight) water solution of trehalose.
2. Put a magnetic mixer in isolated dispergation vessel and cover with conic cover with closable portholes.
3. Insert an ultrasonic probe (120 kHz) in the vessel through one of the portholes and attach the vessel to the magnetic mixer table.
4. After filling the vessel up to the edge with liquid nitrogen put the cover on the vessel and let the liquid still.
5. Squirt approximately 5 ml of the solution on the nitrogen surface and close the cover.
6. Drive 3 ml/min. of water solution of the anti-neoplastic composition 4 and trehalose to the work space by a peristaltic pump through another porthole and switch on the magnetic mixer.
7. After dispergation transfer the produced solid particles of the solution to Class I clear glass vials and close them provisionally with lyophilizing plug at normal temperature.
8. Put the vials on partitions of the freeze-dryer (GFT 6, Klein Vakuumtechnik, Niederfishbach, DE) and reduce pressure to 80 kPa.

9. Cool the vials gradually to 0° C. for 3 hours, then to −35° C. for 12 hours, primary drying is performed by temperature increase to −10° C. for 8 hours and to 10° C. for 8 hours.
10. After temperature rise to 30° C. during 1 hour secondary drying continues at 30° C. for 6 hours at pressure 10 kPa.
11. After tempering the product to normal temperature fill the freeze-dryer with sterilized air and close the vials with the lyophilised product.

The obtained powder is prepared for processing, filling and application in dose powder inhaler (e.g. of Turbhaler, Easyhaler, Novolizer, Certihaler type) or as pressurized powder (e.g. in Ultrahaler or MAG-haler type inhalers), or in a single-dose system with pre-adjusted powder capsules (e.g. Spinhaler, Aerolizerk, Handihaler), or powders in multi-dose capsule or blister systems (e.g. Diskhaler or Diskus).

Example 13: Preparation with Anti-Neoplastic Composition 4 for Human Laryngeal Carcinoma Treatment for Inhalation Administration by Nebuliser Powder formula (g) for nebulisation of 10 doses (g):

| | |
|---|---|
| Composition 4 | 0.482 g |
| Trehalosa | 5.50 |

The powder composition for reconstitution for inhalation is aseptically distributed in ten glass injection bottles to 100 ml while the content of Composition 4 is 48.2 mg.

For the reconstitution 1 bottle is filled with water for injection or sterilized water. Nebulisation is performed in a suitable small e.g. jet based, vibrating membrane or electronic nebuliser of e.g. Spag-2, PARI LC Star, Aero-Eclipse or Pro-Dose type.

Example 13. Preparation for Intraperitoneal Administration for Mammary Carcinoma Treatment in a Dog or a Cat Formula (g) for 100 doses

| | | |
|---|---|---|
| Composition 5 | 2.239 | (see Tab. 1) |
| Trehalose | 20.00 | |

The above Formula is processed as mixture lyophilised powder containing Composition 5 according to Table 1 and structural stabilizing trehalose distributed into 100 vials.

It is administered in one dose as eutonic-isotonic water solution after reconstitution ex tempore from dry powder in 5% glucose solution.

Specific dosage of the composition is based on complex oncologic examination of particular individual.

The invention claimed is:

1. A method for treating cancerous tumors, metastases, or both, wherein said method comprises administering a pharmaceutical composition comprising a mixture of proenzymes and enzymes, wherein the composition consists of:
proenzymes trypsinogen and chymotrypsinogen; and
enzymes *Bacillus* species α-amylase (α-amylase B.s, A) and *Triticum aestivum* lipase (lipase T.a., L);
wherein a ratio of enzymatic activities of trypsinogen (T), chymotrypsinogen A (CH), α-amylase, and lipase T:CH:A:L expressed in international units (i.u.) are in a range of from 150:150:40:1 to 400:1200:200:1; and one or more pharmaceutically acceptable excipients, for simultaneous, separate, and sequential parenteral or transmucosal administration of the composition.

2. The method according to claim 1, wherein the trypsinogen is type I trypsinogen.

3. The method according to claim 1, wherein minimum enzymatic activities of trypsinogen, chymotrypsinogen, α-amylase, and lipase are: trypsinogen 40 i.u./mg, chymotrypsinogen 60 i.u./mg, α-amylase 20 i.u./mg, and lipase 1 i.u./mg.

4. The method according to claim 1, wherein at least one of the trypsinogen, chymotrypsinogen, α-amylase, and lipase is replaced with a biologically similar active substance, wherein an amino acid sequence of the mold, yeast, or bacterial biologically similar active substance is at least 90% identical to an amino acid sequence of the replaced trypsinogen, chymotrypsinogen, α-amylase, and lipase.

5. The method according to claim 1, wherein the composition is administered by systemic, sublingual, rectal, inhalation, or parenteral administration.

6. The method according to claim 1, wherein the one or more pharmaceutically acceptable excipients comprise:
one or more hydrophilic polyhydric alcohols,
hydrophilic low molecular alcohols,
saccharides,
polysorbates,
poloxamers,
one or more lipophilic excipients,
esters of higher fatty acids with glycerol or propylene glycol,
esters of lower monovalent alcohols,
esters of higher fatty acids with medium and higher fatty alcohols,
higher fatty alcohols and analogously higher fatty acids,
vegetable oils,
phospholipids,
sterols,
biocompatible and biodegradable polymers, or
any combination thereof.

7. The method according to claim 6, wherein the one or more hydrophilic polyhydric alcohols include polyethylene glycol with a molecular weight of between 100 to 8,000.

8. The method according to claim 6, wherein the hydrophilic low molecular alcohols are selected from glycerol, propylene glycol, n-propanol, or any combination thereof.

9. The method according to claim 6, wherein the saccharides are selected from trehalose, mannitol, lactose, sorbitol, myoinositol, or any combination thereof.

10. The method according to claim 6, wherein the polysorbates are selected from polysorbate 20, polysorbate 60, polysorbate 80, or any combination thereof.

11. The method according to claim 6, wherein the poloxamers are selected from poloxamer 182, poloxamer 417, poloxamer 908, or any combination thereof.

12. The method according to claim 6, wherein the one or more lipophilic excipients include hydrogenated triglycerides selected from hydrogenated glycerol trioleate, hydrogenated glycerol cocoate, or any combination thereof.

13. The method according to claim 6, wherein the esters of higher fatty acids with glycerol or propylene glycol are selected from the group consisting of glycerol tripalmitate, glycerol trioleate, glycerol tristearate, glycerol distearate, glycerol dioleate, glycerol monolaurate, propylene glycol myristate, glycerol dipalmitostearate, or any combination thereof.

14. The method according to claim 6, wherein the esters of lower monovalent alcohols are selected from diisopropyl adipate, isopropyl laurate, isopropyl linoleate, isopropyl palmitate, or any combinations thereof.

15. The method according to claim 6, wherein the esters of higher fatty acids with medium and higher fatty alcohols include myristyl stearate, capryl stearate, cetyl palmitate, caprin behenate, lauroyl oleate, or any combination thereof.

16. The method according to claim 6, wherein the higher fatty alcohols are selected from lauryl alcohol, myristyl alcohol, palmityl alcohol, stearyl alcohol, behenyl alcohol and the analogous higher fatty acids is selected from lauric, myristic, palmitic, stearic, lignoceric, arachidonic, behenic acids and their ethoxylated derivatives, selected from polyethylene glycol 10 oleyl alcohol, polyethylene glycol 25 stearyl alcohol, polyethylene glycol 40 stearyl alcohol, stearoyl polyethylene glycol 32 glycerol, polyethylene glycol 15 hydroxy stearate, or any combination thereof.

17. The method according to claim 6, wherein the vegetable oils are selected from cottonseed oil, sunflower oil, groundnut oil, soya oil, castor oil, and their ethoxylated derivatives selected from polyoxyl 35 ricinoleate, or any combination thereof.

18. The method according to claim 6, wherein the phospholipids are selected from egg lecithin, soya lecithin, dioleoylphosphatidylcholine, dipalmitoylphosphatidylserine, or any combination thereof.

19. The method according to claim 6, wherein the sterols are selected from cholesterol and its derivatives selected from cholesteryl linoleate, cholesteryl acetate, or any combination thereof.

20. The method according to claim 6, wherein the biocompatible and biodegradable polymers are selected from polyesters selected from poly-DL-lactic acid (PDLLA), polyglycolic acid (PGA), poly-DL-lactic glycolic acid (PLGA), or any combination thereof.

21. The method according to claim 1, wherein the composition is administered by sublingual administration, wherein the composition is in the form of nanofibers and comprises:
at least one of polyvinyl polymers selected from the group consisting of polyvinylpyrrolidone with molecular weight approx. 30,000 to 50,000 and polyvinyl alcohols with molecular weight from 20,000 to 200,000;
cellulose derivatives selected from the group consisting of methylcellulose, hydroxypropyl methylcellulose, and hydroxypropyl cellulose; and/or
starch type polysaccharides selected from the group consisting of hydroxyethyl starch and carboxymethyl starch sodium salt; and/or dextrins with molecular weight from 4,000 to 80,000;
and/or dextran type biotechnological polysaccharides with molecular weight from 10,000 to 80,000;
and/or glucuronate type substances wherein the glucuronate type substances is xanthan mucilage; and/or further polyuronides or their salts selected from the group consisting of sodium and potassium, hyaluronans, alginans, pectinans, and arabinans; and/or acrylic or methacrylic acid polymers and/or their copolymers selected from the group consisting of carboxyvinyl polymers cross-linked with polyalkenyl ethers of sugars or polyalcohols selected from the group consisting of diallyl sucrose a diallyl pentaerythritol, α-hydroxy acid biodegradable polyesters selected from the group consisting of poly-DL-lactic acid (PDLLA), polyglycolic acid (PGA), poly-DL-lactic glycolic acid (PLGA), polycaprolactones with molecular weight from 10,000 to 100,000, and/or copolymer type polymeric excipients, wherein the excipient is polyvinyl caprolactam-polyvinyl acetate polyethylene glycol.

22. The method according to claim 1, wherein the composition is administered by inhalation, wherein the composition contains at least one or more saccharides selected from the group consisting of trehalose, mannitol, glucose, and/or various forms of lactose.

23. The method according to claim 1, wherein the composition is in the form of a nanofiber stabilized preparation for direct administration or a stabilized storage intermediate product or final preparation.

* * * * *

SEQUENCE LISTING

<160> NUMBER OF SEQ ID NOS: 13

<210> SEQ ID NO 1
<211> LENGTH: 513
<212> TYPE: PRT
<213> ORGANISM: Bacillus amyloliquefaciens

<400> SEQUENCE: 1

Met Ile Gln Lys Arg Lys Arg Thr Val Ser Phe Arg Leu Val Leu Met
1               5                   10                  15

Cys Thr Leu Leu Phe Val Ser Leu Pro Ile Thr Lys Thr Ser Ala Val
            20                  25                  30

Asn Gly Thr Leu Met Gln Tyr Phe Glu Trp Tyr Thr Pro Asn Asp Gly
        35                  40                  45

Gln His Trp Lys Arg Leu Gln Asn Asp Ala Glu His Leu Ser Asp Ile
    50                  55                  60

Gly Ile Thr Ala Val Trp Ile Pro Pro Ala Tyr Lys Gly Leu Ser Gln
65                  70                  75                  80

Ser Asp Asn Gly Tyr Gly Pro Tyr Asp Leu Tyr Asp Leu Gly Glu Phe
                85                  90                  95

Gln Gln Lys Gly Thr Val Arg Thr Lys Tyr Gly Thr Lys Ser Glu Leu
            100                 105                 110

Gln Asp Ala Ile Gly Ser Leu His Ser Arg Asn Val Gln Val Tyr Gly
        115                 120                 125

Asp Val Val Leu Asn His Lys Ala Gly Ala Asp Ala Thr Glu Asp Val
    130                 135                 140

Thr Ala Val Glu Val Asn Pro Ala Asn Arg Asn Gln Glu Thr Ser Glu
145                 150                 155                 160

Glu Tyr Gln Ile Lys Ala Trp Thr Asp Phe Arg Phe Pro Gly Arg Gly

```
            165                 170                 175
Asn Thr Tyr Ser Asp Phe Lys Trp His Trp Tyr His Phe Asp Gly Ala
            180                 185                 190

Asp Trp Asp Glu Ser Arg Lys Ile Ser Arg Ile Phe Lys Phe Arg Gly
            195                 200                 205

Glu Gly Lys Ala Trp Asp Trp Glu Val Ser Ser Glu Asn Gly Asn Tyr
            210                 215                 220

Asp Tyr Leu Met Tyr Ala Asp Val Asp Tyr Asp His Pro Asp Val Val
225                 230                 235                 240

Ala Glu Thr Lys Lys Trp Gly Ile Trp Tyr Ala Asn Glu Leu Ser Leu
            245                 250                 255

Asp Gly Phe Arg Ile Asp Ala Ala Lys His Ile Lys Phe Ser Phe Leu
            260                 265                 270

Arg Asp Trp Val Gln Ala Val Arg Gln Ala Thr Gly Lys Glu Met Phe
            275                 280                 285

Thr Val Ala Glu Tyr Trp Gln Asn Asn Ala Gly Lys Leu Glu Asn Tyr
            290                 295                 300

Leu Asn Lys Thr Ser Phe Asn Gln Ser Val Phe Asp Val Pro Leu His
305                 310                 315                 320

Phe Asn Leu Gln Ala Ala Ser Ser Gln Gly Gly Tyr Asp Met Arg
            325                 330                 335

Arg Leu Leu Asp Gly Thr Val Val Ser Arg His Pro Glu Lys Ala Val
            340                 345                 350

Thr Phe Val Glu Asn His Asp Thr Gln Pro Gly Gln Ser Leu Glu Ser
            355                 360                 365

Thr Val Gln Thr Trp Phe Lys Pro Leu Ala Tyr Ala Phe Ile Leu Thr
            370                 375                 380

Arg Glu Ser Gly Tyr Pro Gln Val Phe Tyr Gly Asp Met Tyr Gly Thr
385                 390                 395                 400

Lys Gly Thr Ser Pro Lys Glu Ile Pro Ser Leu Lys Asp Asn Ile Glu
            405                 410                 415

Pro Ile Leu Lys Ala Arg Lys Glu Tyr Ala Tyr Gly Pro Gln His Asp
            420                 425                 430

Tyr Ile Asp His Pro Asp Val Ile Gly Trp Thr Arg Glu Gly Asp Ser
            435                 440                 445

Ser Ala Ala Lys Ser Gly Leu Ala Ala Leu Ile Thr Asp Gly Pro Gly
            450                 455                 460

Gly Ser Lys Arg Met Tyr Ala Gly Leu Lys Asn Ala Gly Glu Thr Trp
465                 470                 475                 480

Tyr Asp Ile Thr Gly Asn Arg Ser Asp Thr Val Lys Ile Gly Ser Asp
            485                 490                 495

Gly Trp Gly Glu Phe His Val Asn Asp Gly Ser Val Ser Ile Tyr Val
            500                 505                 510

Gln

<210> SEQ ID NO 2
<211> LENGTH: 350
<212> TYPE: PRT
<213> ORGANISM: Triticum urartu

<400> SEQUENCE: 2

Met Glu Arg Arg Gly Leu Leu Lys Ala Ala Leu Leu Ala Ser Cys Leu
1               5                   10                  15

Leu Val Val Cys Ser Gly Arg Val Pro Thr Val Ile Gln Gln Pro Ser
```

```
            20                  25                  30
Thr Thr Ile Tyr Asn Ser Thr Leu Ala Lys Thr Leu Val Glu Tyr Ala
            35                  40                  45
Ala Ala Ile Tyr Thr Ala Asp Leu Thr Gln Leu Phe Thr Trp Thr Cys
            50                  55                  60
Asp Arg Cys Gly Asp Leu Ile Glu Gly Phe Glu Met Met Asp Ile Ile
 65                  70                  75                  80
Val Asp Val Glu Ser Cys Leu Glu Ala Tyr Val Gly Phe Ala Ser Asp
                     85                  90                  95
Ile Asn Ala Val Val Val Phe Arg Gly Thr Gln Glu Asn Ser Ile
                100                 105                 110
Gln Asn Trp Ile Glu Asp Leu Leu Trp Lys Gln Leu Asp Leu Asp Tyr
                115                 120                 125
Pro Gly Met Pro Glu Ala Met Val His Arg Gly Phe Tyr Ser Ala Tyr
                130                 135                 140
His Asn Thr Thr Ile Arg Asp Gly Ile Val Ser Gly Ile Gln Lys Thr
145                 150                 155                 160
Gln Lys Leu His Gly Asp Val Pro Ile Met Val Thr Gly His Ser Met
                165                 170                 175
Gly Ala Ala Met Ala Ser Phe Cys Ala Leu Asp Leu Val Val Asn Tyr
                180                 185                 190
Gly Leu Asp Asp Val Lys Leu Met Thr Phe Gly Gln Pro Arg Val Gly
                195                 200                 205
Asn Ala Ala Phe Ala Ser Tyr Leu Lys Arg Tyr Leu Pro His Ala Ile
                210                 215                 220
Arg Val Thr Asn Ala Asn Asp Ile Val Pro His Leu Pro Pro Tyr Phe
225                 230                 235                 240
Ser Phe Phe Pro Gln Lys Thr Tyr His His Phe Pro Arg Glu Val Trp
                245                 250                 255
Val His Asp Val Gly Leu Gly Ser Leu Val Tyr Thr Val Glu Gln Ile
                260                 265                 270
Cys Asp Asp Ser Gly Glu Asp Pro Ala Cys Ser Arg Ser Val Ser Gly
                275                 280                 285
Asn Ser Ile Gln Asp His Ile Thr Tyr Leu Gly Val Ser Met His Ala
                290                 295                 300
Glu Ala Trp Ser Ser Cys Arg Ile Val Met Asp Tyr Ala Glu Leu Arg
305                 310                 315                 320
Tyr Lys Met Asp Leu His Gly Asn Val Val Leu Ser Lys Gln Gln Gln
                325                 330                 335
Gln Ser Gly Leu Ser Asn Glu Arg Arg His Ser Ala Gln
                340                 345                 350

<210> SEQ ID NO 3
<211> LENGTH: 512
<212> TYPE: PRT
<213> ORGANISM: Bacillus licheniformis

<400> SEQUENCE: 3

Met Lys Gln Gln Lys Arg Leu Tyr Ala Arg Leu Leu Thr Leu Leu Phe
 1               5                  10                  15
Ala Leu Ile Phe Leu Leu Pro His Ser Ala Ala Ala Ala Ala Asn Leu
                20                  25                  30
Asn Gly Thr Leu Met Gln Tyr Phe Glu Trp Tyr Met Pro Asn Asp Gly
                35                  40                  45
```

```
Gln His Trp Lys Arg Leu Gln Asn Asp Ser Ala Tyr Leu Ala Glu His
    50                  55                  60

Gly Ile Thr Ala Val Trp Ile Pro Pro Ala Tyr Lys Gly Thr Ser Gln
65                  70                  75                  80

Ala Asp Val Gly Tyr Gly Ala Tyr Asp Leu Tyr Asp Leu Gly Glu Phe
                85                  90                  95

His Gln Lys Gly Thr Val Arg Thr Lys Tyr Gly Thr Lys Gly Glu Leu
            100                 105                 110

Gln Ser Ala Ile Lys Ser Leu His Ser Arg Asp Ile Asn Val Tyr Gly
        115                 120                 125

Asp Val Val Ile Asn His Lys Gly Gly Ala Asp Ala Thr Glu Asp Val
    130                 135                 140

Thr Ala Val Glu Val Asp Pro Ala Asp Arg Asn Arg Val Ile Ser Gly
145                 150                 155                 160

Glu His Arg Ile Lys Ala Trp Thr His Phe His Phe Pro Gly Arg Gly
                165                 170                 175

Ser Thr Tyr Ser Asp Phe Lys Trp His Trp Tyr His Phe Asp Gly Thr
            180                 185                 190

Asp Trp Asp Glu Ser Arg Lys Leu Asn Arg Ile Tyr Lys Phe Gln Gly
    195                 200                 205

Lys Ala Trp Asp Trp Glu Val Ser Asn Glu Asn Gly Asn Tyr Asp Tyr
210                 215                 220

Leu Met Tyr Ala Asp Ile Asp Tyr Asp His Pro Asp Val Ala Ala Glu
225                 230                 235                 240

Ile Lys Arg Trp Gly Thr Trp Tyr Ala Asn Glu Leu Gln Leu Asp Gly
                245                 250                 255

Phe Arg Leu Asp Ala Val Lys His Ile Lys Phe Ser Phe Leu Arg Asp
            260                 265                 270

Trp Val Asn His Val Arg Glu Lys Thr Gly Lys Glu Met Phe Thr Val
    275                 280                 285

Ala Glu Tyr Trp Gln Asn Asp Leu Gly Ala Leu Glu Asn Tyr Leu Asn
290                 295                 300

Lys Thr Asn Phe Asn His Ser Val Phe Asp Val Pro Leu His Tyr Gln
305                 310                 315                 320

Phe His Ala Ala Ser Thr Gln Gly Gly Gly Tyr Asp Met Arg Lys Leu
                325                 330                 335

Leu Asn Ser Thr Val Val Ser Lys His Pro Leu Lys Ala Val Thr Phe
            340                 345                 350

Val Asp Asn His Asp Thr Gln Pro Gly Gln Ser Leu Glu Ser Thr Val
    355                 360                 365

Gln Thr Trp Phe Lys Pro Leu Ala Tyr Ala Phe Ile Leu Thr Arg Glu
370                 375                 380

Ser Gly Tyr Pro Gln Val Phe Tyr Gly Asp Met Tyr Gly Thr Lys Gly
385                 390                 395                 400

Asp Ser Gln Arg Glu Ile Pro Ala Leu Lys His Lys Ile Glu Pro Ile
                405                 410                 415

Leu Lys Ala Arg Lys Gln Tyr Ala Tyr Gly Ala Gln His Asp Tyr Phe
            420                 425                 430

Asp His His Asp Ile Val Gly Trp Thr Arg Glu Gly Asp Ser Ser Val
    435                 440                 445

Ala Asn Ser Gly Leu Ala Ala Leu Ile Thr Asp Gly Pro Gly Gly Ala
450                 455                 460

Lys Arg Met Tyr Val Gly Arg Gln Asn Ala Gly Glu Thr Trp His Asp
```

```
                465                 470                 475                 480
Ile Thr Gly Asn Arg Ser Glu Pro Val Val Ile Asn Ser Glu Gly Trp
                    485                 490                 495
Gly Glu Phe His Val Asn Gly Gly Ser Val Ser Ile Tyr Val Gln Arg
                500                 505                 510

<210> SEQ ID NO 4
<211> LENGTH: 350
<212> TYPE: PRT
<213> ORGANISM: Triticum aestivum

<400> SEQUENCE: 4

Met Glu Arg Arg Gly Leu Leu Lys Thr Ala Leu Leu Ala Cys Leu Leu
1               5                   10                  15
Val Val Cys Ser Gly Arg Val Pro Met Val Ile Gln Gln Pro Ser Thr
                20                  25                  30
Thr Ile Tyr Asn Ser Thr Leu Ala Lys Thr Leu Val Glu Tyr Ala Ala
            35                  40                  45
Ala Ile Tyr Thr Ala Asp Leu Thr Gln Leu Phe Thr Trp Thr Cys Asp
        50                  55                  60
Arg Cys Gly Asp Leu Ile Glu Gly Phe Glu Met Met Asp Ile Ile Val
65                  70                  75                  80
Asp Val Glu Asn Cys Leu Glu Ala Tyr Val Gly Phe Ala Ser Asp Ile
                85                  90                  95
Asn Ala Val Ile Val Val Phe Arg Gly Thr Gln Glu Asn Ser Ile Gln
            100                 105                 110
Asn Trp Ile Glu Asp Leu Leu Trp Lys Gln Leu Asp Leu Asp Tyr Pro
        115                 120                 125
Gly Met Pro Glu Ala Met Val His Arg Gly Phe Tyr Ser Ala Tyr His
    130                 135                 140
Asn Thr Thr Ile Arg Asp Gly Ile Val Ser Gly Ile Gln Lys Thr Arg
145                 150                 155                 160
Lys Leu His Gly Asp Val Pro Ile Met Val Thr Gly His Ser Met Gly
                165                 170                 175
Ala Ala Met Ala Ser Phe Cys Ala Leu Asp Leu Val Val Asn Tyr Gly
            180                 185                 190
Leu Asp Asp Val Lys Leu Met Thr Phe Gly Gln Pro Arg Val Gly Asn
        195                 200                 205
Ala Ala Phe Ala Ser Tyr Phe Lys Arg Tyr Leu Pro His Ala Ile Arg
    210                 215                 220
Val Thr Asn Ala Asn Asp Ile Val Pro His Leu Pro Pro Tyr Phe Ser
225                 230                 235                 240
Phe Phe Pro Gln Lys Ala Tyr His His Phe Pro Arg Glu Val Trp Val
                245                 250                 255
His Asp Val Gly Leu Gly Ser Leu Val Tyr Thr Val Glu Gln Ile Cys
            260                 265                 270
Asp Asp Ser Gly Glu Asp Pro Ala Cys Ser Arg Ser Val Ser Gly Asn
        275                 280                 285
Ser Ile Gln Asp His Ile Thr Tyr Leu Gly Val Ser Met His Ala Glu
    290                 295                 300
Ala Trp Ser Ser Cys Arg Ile Val Met Asp Tyr Ala Glu Leu Arg Tyr
305                 310                 315                 320
Lys Met Asp Leu His Gly Asn Val Val Leu Ser Lys Gln Gln Gln Gln
                325                 330                 335
```

```
Gln Pro Gly Leu Ser Asp Gln Arg Arg Arg His Ser Ala Gln
            340                 345                 350
```

<210> SEQ ID NO 5
<211> LENGTH: 450
<212> TYPE: PRT
<213> ORGANISM: Sus scrofa

<400> SEQUENCE: 5

```
Ser Glu Val Cys Phe Pro Arg Leu Gly Cys Phe Ser Asp Asp Ala Pro
1               5                   10                  15

Trp Ala Gly Ile Val Gln Arg Pro Leu Lys Ile Leu Pro Trp Ser Pro
            20                  25                  30

Lys Asp Val Asp Thr Arg Phe Leu Leu Tyr Thr Asn Gln Asn Gln Asn
        35                  40                  45

Asn Tyr Gln Glu Leu Val Ala Asp Pro Ser Thr Ile Thr Asn Ser Asn
    50                  55                  60

Phe Arg Met Asp Arg Lys Thr Arg Phe Ile Ile His Gly Phe Ile Asp
65                  70                  75                  80

Lys Gly Glu Glu Asp Trp Leu Ser Asn Ile Cys Lys Asn Leu Phe Lys
                85                  90                  95

Val Glu Ser Val Asn Cys Ile Cys Val Asp Trp Lys Gly Gly Ser Arg
            100                 105                 110

Thr Gly Tyr Thr Gln Ala Ser Gln Asn Ile Arg Ile Val Gly Ala Glu
        115                 120                 125

Val Ala Tyr Phe Val Glu Val Leu Lys Ser Ser Leu Gly Tyr Ser Pro
    130                 135                 140

Ser Asn Val His Val Ile Gly His Ser Leu Gly Ser His Ala Ala Gly
145                 150                 155                 160

Glu Ala Gly Arg Arg Thr Asn Gly Thr Ile Glu Arg Ile Thr Gly Leu
                165                 170                 175

Asp Pro Ala Glu Pro Cys Phe Gln Gly Thr Pro Glu Leu Val Arg Leu
            180                 185                 190

Asp Pro Ser Asp Ala Lys Phe Val Asp Val Ile His Thr Asp Ala Ala
        195                 200                 205

Pro Ile Ile Pro Asn Leu Gly Phe Gly Met Ser Gln Thr Val Gly His
    210                 215                 220

Leu Asp Phe Phe Pro Asn Gly Gly Lys Gln Met Pro Gly Cys Gln Lys
225                 230                 235                 240

Asn Ile Leu Ser Gln Ile Val Asp Ile Asp Gly Ile Trp Glu Gly Thr
                245                 250                 255

Arg Asp Phe Val Ala Cys Asn His Leu Arg Ser Tyr Lys Tyr Tyr Ala
            260                 265                 270

Asp Ser Ile Leu Asn Pro Asp Gly Phe Ala Gly Phe Pro Cys Asp Ser
        275                 280                 285

Tyr Asn Val Phe Thr Ala Asn Lys Cys Phe Pro Cys Pro Ser Glu Gly
    290                 295                 300

Cys Pro Gln Met Gly His Tyr Ala Asp Arg Phe Pro Gly Lys Thr Asn
305                 310                 315                 320

Gly Val Ser Gln Val Phe Tyr Leu Asn Thr Gly Asp Ala Ser Asn Phe
                325                 330                 335

Ala Arg Trp Arg Tyr Lys Val Ser Val Thr Leu Ser Gly Lys Lys Val
            340                 345                 350

Thr Gly His Ile Leu Val Ser Leu Phe Gly Asn Glu Gly Asn Ser Arg
        355                 360                 365
```

Gln Tyr Glu Ile Tyr Lys Gly Thr Leu Gln Pro Asn Thr His Ser
        370                 375                 380

Asp Glu Phe Asp Ser Asp Val Glu Val Gly Asp Leu Gln Lys Val Lys
385                 390                 395                 400

Phe Ile Trp Tyr Asn Asn Val Ile Asn Pro Thr Leu Pro Arg Val
                405                 410                 415

Gly Ala Ser Lys Ile Thr Val Glu Arg Asn Asp Gly Lys Val Tyr Asp
            420                 425                 430

Phe Cys Ser Gln Glu Thr Val Arg Glu Val Leu Leu Thr Leu Asn
            435                 440                 445

Pro Cys
    450

<210> SEQ ID NO 6
<211> LENGTH: 407
<212> TYPE: PRT
<213> ORGANISM: Oryza sativa

<400> SEQUENCE: 6

Met Ser Ser Ser Pro Met Leu Gly Gly Ile Ala Asp Arg Trp Arg Glu
1               5                   10                  15

Leu His Gly Gln Asp Ser Trp Asn Gly Leu Leu Asp Pro Leu Asp Leu
            20                  25                  30

Asp Leu Arg Ser Ser Ile Leu Ser Tyr Gly Glu Leu Val Gln Ala Thr
        35                  40                  45

Tyr Asp Ser Phe Asn Arg Glu Arg Ser Pro His Ala Gly Ala Cys
    50                  55                  60

Val Tyr Gly His Gly Asp Leu Leu Ala Ala Gly Ala Ser Ala Ala
65              70                  75                  80

Gly Ser Tyr Ala Val Thr Lys Phe Val Tyr Ala Thr Ser Gly Leu Pro
                85                  90                  95

Val Pro Glu Ala Phe Leu Leu Leu Pro Leu Pro Ser Leu Leu Pro
            100                 105                 110

Ala Trp Ser Arg Glu Ser Asn Trp Met Gly Tyr Val Ala Val Ala Thr
        115                 120                 125

Asp Glu Gly Val Ala Ala Leu Gly Arg Arg Asp Ile Val Val Ala Trp
    130                 135                 140

Arg Gly Thr Val Glu Ser Leu Glu Trp Val Asn Asp Phe Asp Phe Thr
145                 150                 155                 160

Pro Val Pro Ala Ala Pro Val Leu Gly Ala Ala Ala Ala Asn Pro
                165                 170                 175

Arg Ala Ile Val His Arg Gly Phe Leu Ser Val Tyr Thr Ser Ser Asn
            180                 185                 190

Lys Asp Ser Lys Tyr Asn Lys Ala Ser Ala Arg Asp Gln Val Leu Glu
        195                 200                 205

Glu Val Arg Arg Leu Met Glu Leu Tyr Lys Asp Glu Val Thr Ser Ile
    210                 215                 220

Thr Val Val Gly His Ser Leu Gly Ala Ser Leu Ala Thr Leu Asn Ala
225                 230                 235                 240

Val Asp Ile Val Ala Asn Gly Ala Asn Cys Pro Pro Ala Ser Ser Ser
                245                 250                 255

Ser Ser Gln Pro Pro Cys Pro Val Thr Ala Ile Val Phe Ala Ser Pro
            260                 265                 270

Arg Val Gly Asp Gly Phe Phe Lys Ala Ala Phe Ala Ser Phe Pro Asp

```
                275                 280                 285
Leu Arg Ala Leu His Val Lys Asn Ala Gly Asp Val Pro Met Tyr
    290                 295                 300
Pro Pro Leu Gly Tyr Val Asp Val Ala Val Lys Leu Arg Ile Ser Thr
305                 310                 315                 320
Ser Arg Ser Pro Tyr Leu Arg Ser Pro Gly Thr Ile Glu Thr Leu His
                325                 330                 335
Asn Leu Glu Cys Tyr Leu His Gly Val Ala Gly Glu Gln Gly Ser Ala
                340                 345                 350
Gly Gly Phe Lys Leu Glu Val Asp Arg Asp Val Ala Leu Ala Asn Lys
            355                 360                 365
Gly Val Asp Ala Leu Lys Asp Lys Tyr Pro Val Pro Pro Arg Trp Trp
        370                 375                 380
Val Ser Lys Asn Arg Cys Met Val Lys Asp Ala Asp Gly His Trp Ala
385                 390                 395                 400
Leu His Asp Phe Glu Gln Ile
            405
```

<210> SEQ ID NO 7
<211> LENGTH: 357
<212> TYPE: PRT
<213> ORGANISM: Bifidobacterium animalis

<400> SEQUENCE: 7

```
Met Glu Leu Tyr Arg Asn Asn Glu Ile Pro Pro Ile Glu Tyr Thr Pro
1               5                   10                  15
Gly Thr Ser Glu Phe Arg Asp Ala Val Ile Gly Leu Ala Arg Tyr Trp
                20                  25                  30
Thr Ala Ile Ala Glu Asp Leu His Ala Asp Glu Pro Gly Val Gln Glu
            35                  40                  45
Arg Thr Ala Ala Ala Cys Leu Arg Phe Arg Lys Glu Cys Ala Met Phe
    50                  55                  60
Asp Tyr Ala Arg Ala Leu Gln Trp His Asp Pro Gln Gly Val Tyr Val
65                  70                  75                  80
His Thr Asp Ile Pro Tyr Leu Pro Asp Gly Tyr Arg Asp Gly Glu
                85                  90                  95
Val Arg Gly His Leu Leu Asp Val Tyr Ile Pro Arg Asp Ala Ile Val
                100                 105                 110
Arg Gly Gly Asn Thr Leu Pro Val Tyr Ile Asp Ile His Gly Gly Gly
            115                 120                 125
Phe Thr Tyr Gly Tyr Lys Glu Leu Asn Arg Asn Phe Asn Thr His Leu
    130                 135                 140
Ala Asp Leu Gly Phe Gly Val Phe Ser Leu Asn Tyr Arg Pro Ala Pro
145                 150                 155                 160
Gln Thr Asp Leu Val Gly Gln Leu His Asp Ile Gln Ala Ala Leu Cys
                165                 170                 175
Trp Ile Gly Glu His Ile Thr Gln Phe Pro Val Ser Pro Asp Asn Ile
                180                 185                 190
Phe Ile Thr Gly Asp Ser Ala Gly Ala Cys Leu Ser Leu Leu Thr Leu
            195                 200                 205
Leu Ile Glu His Asn Asp Asp Ala Ala His Ala Phe Gly Ile Glu Arg
    210                 215                 220
Ala Ser Gly Ile His Leu Arg Gly Ala Ser Leu Ile Ser Gly Val Tyr
225                 230                 235                 240
```

```
Asp Ile Thr Pro Ser Ser Pro Met Arg Ala Arg Leu Ala Glu Thr Val
                245                 250                 255

Gly Asn Glu Phe Phe Ala Gly Leu Asp Asp Ala Thr Val Phe Leu Asp
            260                 265                 270

Pro Ala Asp Trp Leu Thr Gln Gly Ile Gly Ile Pro Pro Leu Phe Leu
        275                 280                 285

Val Thr Ser Ser Asp Phe Val Gln Ser Glu Thr Leu Ala Leu Ala
    290                 295                 300

Thr Ser Leu Ala Arg Asn Gly Arg Asp Phe Glu Leu His Asp Phe Lys
305                 310                 315                 320

Val Pro Cys Thr Gln Thr Leu Gly His Val Phe Pro Val Gly Met Thr
                325                 330                 335

Trp Leu Pro Glu Ser Glu Arg Val Leu His Gly Ile Arg Glu Phe Ser
            340                 345                 350

Tyr Pro Leu Thr Arg
            355

<210> SEQ ID NO 8
<211> LENGTH: 229
<212> TYPE: PRT
<213> ORGANISM: Bos taurus

<400> SEQUENCE: 8

Val Asp Asp Asp Lys Ile Val Gly Gly Tyr Thr Cys Gly Ala Asn
1               5                   10                  15

Thr Val Pro Tyr Gln Val Ser Leu Asn Ser Gly Tyr His Phe Cys Gly
                20                  25                  30

Gly Ser Leu Ile Asn Ser Gln Trp Val Val Ser Ala Ala His Cys Tyr
            35                  40                  45

Lys Ser Gly Ile Gln Val Arg Leu Gly Glu Asp Asn Ile Asn Val Val
        50                  55                  60

Glu Gly Asn Glu Gln Phe Ile Ser Ala Ser Lys Ser Ile Val His Pro
65                  70                  75                  80

Ser Tyr Asn Ser Asn Thr Leu Asn Asn Asp Ile Met Leu Ile Lys Leu
                85                  90                  95

Lys Ser Ala Ala Ser Leu Asn Ser Arg Val Ala Ser Ile Ser Leu Pro
            100                 105                 110

Thr Ser Cys Ala Ser Ala Gly Thr Gln Cys Leu Ile Ser Gly Trp Gly
        115                 120                 125

Asn Thr Lys Ser Ser Gly Thr Ser Tyr Pro Asp Val Leu Lys Cys Leu
130                 135                 140

Lys Ala Pro Ile Leu Ser Asp Ser Ser Cys Lys Ser Ala Tyr Pro Gly
145                 150                 155                 160

Gln Ile Thr Ser Asn Met Phe Cys Ala Gly Tyr Leu Glu Gly Gly Lys
                165                 170                 175

Asp Ser Cys Gln Gly Asp Ser Gly Gly Pro Val Val Cys Ser Gly Lys
            180                 185                 190

Leu Gln Gly Ile Val Ser Trp Gly Ser Gly Cys Ala Gln Lys Asn Lys
        195                 200                 205

Pro Gly Val Tyr Thr Lys Val Cys Asn Tyr Val Ser Trp Ile Lys Gln
    210                 215                 220

Thr Ile Ala Ser Asn
225

<210> SEQ ID NO 9
```

```
<211> LENGTH: 245
<212> TYPE: PRT
<213> ORGANISM: Bos taurus

<400> SEQUENCE: 9

Cys Gly Val Pro Ala Ile Gln Pro Val Leu Ser Gly Leu Ser Arg Ile
1               5                   10                  15

Val Asn Gly Glu Glu Ala Val Pro Gly Ser Trp Pro Trp Gln Val Ser
            20                  25                  30

Leu Gln Asp Lys Thr Gly Phe His Phe Cys Gly Gly Ser Leu Ile Asn
        35                  40                  45

Glu Asn Trp Val Val Thr Ala Ala His Cys Gly Val Thr Thr Ser Asp
    50                  55                  60

Val Val Val Ala Gly Glu Phe Asp Gln Gly Ser Ser Ser Glu Lys Ile
65                  70                  75                  80

Gln Lys Leu Lys Ile Ala Lys Val Phe Lys Asn Ser Lys Tyr Asn Ser
                85                  90                  95

Leu Thr Ile Asn Asn Asp Ile Thr Leu Leu Lys Leu Ser Thr Ala Ala
            100                 105                 110

Ser Phe Ser Gln Thr Val Ser Ala Val Cys Leu Pro Ser Ala Ser Asp
        115                 120                 125

Asp Phe Ala Ala Gly Thr Thr Cys Val Thr Thr Gly Trp Gly Leu Thr
    130                 135                 140

Arg Tyr Thr Asn Ala Asn Thr Pro Asp Arg Leu Gln Gln Ala Ser Leu
145                 150                 155                 160

Pro Leu Leu Ser Asn Thr Asn Cys Lys Lys Tyr Trp Gly Thr Lys Ile
                165                 170                 175

Lys Asp Ala Met Ile Cys Ala Gly Ala Ser Gly Val Ser Ser Cys Met
            180                 185                 190

Gly Asp Ser Gly Gly Pro Leu Val Cys Lys Lys Asn Gly Ala Trp Thr
        195                 200                 205

Leu Val Gly Ile Val Ser Trp Gly Ser Ser Thr Cys Ser Thr Ser Thr
    210                 215                 220

Pro Gly Val Tyr Ala Arg Val Thr Ala Leu Val Asn Trp Val Gln Gln
225                 230                 235                 240

Thr Leu Ala Ala Asn
                245

<210> SEQ ID NO 10
<211> LENGTH: 245
<212> TYPE: PRT
<213> ORGANISM: Bos taurus

<400> SEQUENCE: 10

Cys Gly Val Pro Ala Ile Gln Pro Val Leu Ser Gly Leu Ser Arg Ile
1               5                   10                  15

Val Asn Gly Glu Glu Ala Val Pro Gly Ser Trp Pro Trp Gln Val Ser
            20                  25                  30

Leu Gln Asp Lys Thr Gly Phe His Phe Cys Gly Gly Ser Leu Ile Asn
        35                  40                  45

Glu Asn Trp Val Val Thr Ala Ala His Cys Gly Val Thr Thr Ser Asp
    50                  55                  60

Val Val Val Ala Gly Glu Phe Asp Gln Gly Ser Ser Ser Glu Lys Ile
65                  70                  75                  80

Gln Lys Leu Lys Ile Ala Lys Val Phe Lys Asn Ser Lys Tyr Asn Ser
                85                  90                  95
```

```
Leu Thr Ile Asn Asn Asp Ile Thr Leu Leu Lys Leu Ser Thr Ala Ala
            100                 105                 110

Ser Phe Ser Gln Thr Val Ser Ala Val Cys Leu Pro Ser Ala Ser Asp
            115                 120                 125

Asp Phe Ala Ala Gly Thr Thr Cys Val Thr Thr Gly Trp Gly Leu Thr
            130                 135                 140

Arg Tyr Thr Asn Ala Asn Thr Pro Asp Arg Leu Gln Gln Ala Ser Leu
145                 150                 155                 160

Pro Leu Leu Ser Asn Thr Asn Cys Lys Lys Tyr Trp Gly Thr Lys Ile
            165                 170                 175

Lys Asp Ala Met Ile Cys Ala Gly Ala Ser Gly Val Ser Ser Cys Met
            180                 185                 190

Gly Asp Ser Gly Gly Pro Leu Val Cys Lys Lys Asn Gly Ala Trp Thr
            195                 200                 205

Leu Val Gly Ile Val Ser Trp Gly Ser Ser Thr Cys Ser Thr Ser Thr
            210                 215                 220

Pro Gly Val Tyr Ala Arg Val Thr Ala Leu Val Asn Trp Val Gln Gln
225                 230                 235                 240

Thr Leu Ala Ala Asn
            245

<210> SEQ ID NO 11
<211> LENGTH: 245
<212> TYPE: PRT
<213> ORGANISM: Bos taurus

<400> SEQUENCE: 11

Cys Gly Val Pro Ala Ile Gln Pro Val Leu Ser Gly Leu Ser Arg Ile
1               5                   10                  15

Val Asn Gly Glu Glu Ala Val Pro Gly Ser Trp Pro Trp Gln Val Ser
            20                  25                  30

Leu Gln Asp Lys Thr Gly Phe His Phe Cys Gly Gly Ser Leu Ile Asn
            35                  40                  45

Glu Asn Trp Val Val Thr Ala Ala His Cys Gly Val Thr Thr Ser Asp
50                  55                  60

Val Val Val Ala Gly Glu Phe Asp Gln Gly Ser Ser Ser Glu Lys Ile
65                  70                  75                  80

Gln Lys Leu Lys Ile Ala Lys Val Phe Lys Asn Ser Lys Tyr Asn Ser
            85                  90                  95

Leu Thr Ile Asn Asn Asp Ile Thr Leu Leu Lys Leu Ser Thr Ala Ala
            100                 105                 110

Ser Phe Ser Gln Thr Val Ser Ala Val Cys Leu Pro Ser Ala Ser Asp
            115                 120                 125

Asp Phe Ala Ala Gly Thr Thr Cys Val Thr Thr Gly Trp Gly Leu Thr
            130                 135                 140

Arg Tyr Thr Asn Ala Asn Thr Pro Asp Arg Leu Gln Gln Ala Ser Leu
145                 150                 155                 160

Pro Leu Leu Ser Asn Thr Asn Cys Lys Lys Tyr Trp Gly Thr Lys Ile
            165                 170                 175

Lys Asp Ala Met Ile Cys Ala Gly Ala Ser Gly Val Ser Ser Cys Met
            180                 185                 190

Gly Asp Ser Gly Gly Pro Leu Val Cys Lys Lys Asn Gly Ala Trp Thr
            195                 200                 205

Leu Val Gly Ile Val Ser Trp Gly Ser Ser Thr Cys Ser Thr Ser Thr
```

```
                210                 215                 220
Pro Gly Val Tyr Ala Arg Val Thr Ala Leu Val Asn Trp Val Gln Gln
225                 230                 235                 240

Thr Leu Ala Ala Asn
                245

<210> SEQ ID NO 12
<211> LENGTH: 263
<212> TYPE: PRT
<213> ORGANISM: Artificial Sequence
<220> FEATURE:
<223> OTHER INFORMATION: Synthetic construct, CDS clone

<400> SEQUENCE: 12

Met Ala Phe Leu Trp Leu Leu Ser Cys Trp Ala Leu Leu Gly Thr Thr
1               5                   10                  15

Phe Gly Cys Gly Val Pro Ala Ile His Pro Val Leu Ser Gly Leu Ser
                20                  25                  30

Arg Ile Val Asn Gly Glu Asp Ala Val Pro Gly Ser Trp Pro Trp Gln
            35                  40                  45

Val Ser Leu Gln Asp Lys Thr Gly Phe His Phe Cys Gly Gly Ser Leu
50                  55                  60

Ile Ser Glu Asp Trp Val Val Thr Ala Ala His Cys Gly Val Arg Thr
65                  70                  75                  80

Ser Asp Val Val Ala Gly Glu Phe Asp Gln Gly Ser Asp Glu Glu
                85                  90                  95

Asn Ile Gln Val Leu Lys Ile Ala Lys Val Phe Lys Asn Pro Lys Phe
            100                 105                 110

Ser Ile Leu Thr Val Asn Asn Asp Ile Thr Leu Leu Lys Leu Ala Thr
        115                 120                 125

Pro Ala Arg Phe Ser Gln Thr Val Ser Ala Val Cys Leu Pro Ser Ala
130                 135                 140

Asp Asp Asp Phe Pro Ala Gly Thr Leu Cys Ala Thr Thr Gly Trp Gly
145                 150                 155                 160

Lys Thr Lys Tyr Asn Ala Asn Lys Thr Pro Asp Lys Leu Gln Gln Ala
                165                 170                 175

Ala Leu Pro Leu Leu Ser Asn Ala Glu Cys Lys Lys Ser Trp Gly Arg
            180                 185                 190

Arg Ile Thr Asp Val Met Ile Cys Ala Gly Ala Ser Gly Val Ser Ser
        195                 200                 205

Cys Met Gly Asp Ser Gly Gly Pro Leu Val Cys Gln Lys Asp Gly Ala
210                 215                 220

Trp Thr Leu Val Gly Ile Val Ser Trp Gly Ser Asp Thr Cys Ser Thr
225                 230                 235                 240

Ser Ser Pro Gly Val Tyr Ala Arg Val Thr Lys Leu Ile Pro Trp Val
                245                 250                 255

Gln Lys Ile Leu Ala Ala Asn
            260

<210> SEQ ID NO 13
<211> LENGTH: 235
<212> TYPE: PRT
<213> ORGANISM: Gadus morhua

<400> SEQUENCE: 13

Met Gly His Glu Val Asp Ser Val Leu Pro Gly Leu Phe Arg Arg Thr
1               5                   10                  15
```

```
Tyr Gly Cys Gly Arg Pro Ala Ile Ser Pro Val Ile Thr Gly Tyr Ser
            20              25              30
Arg Ile Val Asn Gly Glu Glu Ala Val Pro His Ser Trp Ser Trp Gln
        35              40              45
Val Ser Leu Gln Asp Gln Thr Gly Phe His Phe Cys Gly Gly Ser Leu
    50              55              60
Ile Asn Glu Asn Trp Val Val Thr Ala Ala His Cys Asn Val Lys Asn
65              70              75              80
Tyr His Arg Val Val Leu Gly Glu His Asp Arg Ser Ser Asn Ser Glu
            85              90              95
Gly Val Gln Val Met Thr Val Gly Gln Val Phe Lys His Pro Arg Tyr
            100             105             110
Asn Gly Phe Thr Ile Asn Asn Asp Ile Leu Leu Val Lys Leu Ala Thr
            115             120             125
Pro Ala Thr Leu Asn Met Arg Val Ser Pro Val Cys Leu Ala Glu Thr
        130             135             140
Asp Asp Val Phe Glu Gly Gly Met Lys Cys Val Thr Ser Gly Trp Gly
145             150             155             160
Leu Thr Arg Tyr Asn Ala Ala Asp Thr Pro Ala Leu Leu Gln Gln Ala
            165             170             175
Ala Leu Pro Leu Leu Thr Asn Glu Gln Cys Lys Lys Phe Trp Gly Asn
        180             185             190
Lys Ile Ser Asp Leu Met Ile Cys Ala Gly Ala Ala Gly Ala Ser Ser
        195             200             205
Cys Met Gly Asp Ser Gly Gly Pro Leu Val Cys Gln Lys Ala Gly Ser
    210             215             220
Trp Thr Leu Val Gly Ile Val Ser Trp Gly Ser
225             230             235
```